(12) United States Patent
Danaboyina et al.

(10) Patent No.: US 6,630,481 B2
(45) Date of Patent: Oct. 7, 2003

(54) VIOLOGEN LINKED ACRIDINE BASED MOLECULE AND PROCESS FOR THE PREPARATION THEREOF

(75) Inventors: Ramaiah Danaboyina, Kerala (IN); Varghese Eldho Nadukkudy, Kerala (IN); Joseph Joshy, Kerala (IN)

(73) Assignee: Council of Scientific and Industrial Research of India, New Delhi (IN)

( * ) Notice: Subject to any disclaimer, the term of this patent is extended or adjusted under 35 U.S.C. 154(b) by 0 days.

(21) Appl. No.: 09/796,081

(22) Filed: Feb. 28, 2001

(65) Prior Publication Data

US 2003/0045538 A1 Mar. 6, 2003

(51) Int. Cl.⁷ .................. A61K 31/4745; A61K 31/473; C07D 219/02
(52) U.S. Cl. .................. 514/285; 514/297; 546/70; 546/103; 546/104
(58) Field of Search .................. 546/103, 104, 546/70; 514/297, 285

(56) References Cited

FOREIGN PATENT DOCUMENTS

JP          06-230569     *    8/1994

OTHER PUBLICATIONS

Bhattacharya et al., J. Indian Chem. Soc., 1998; 75(10–12):716–724.
Takenaka et al., J. Heterocyclic Chem., 1997; 34(1):123–127.
Ihara et al., Chemical Abstracts, 1996; 124(21):280291z.

* cited by examiner

*Primary Examiner*—Evelyn Mei Huang
(74) *Attorney, Agent, or Firm*—Darby & Darby

(57) ABSTRACT

The present invention provides a series of novel bifunctional molecules based on viologen linked acridine, bisacridine and bisacridinium salts of the general formula 1 (1a, 1b, 1c and 1d) and or pharmaceutically acceptable derivatives thereof, which can be used as phototherapeutic and catalytic photoactivated DNA cleaving agents. These molecules are very stable and exhibit high solubility in buffer at physiological conditions. They undergo strong binding with DNA through intercalation and groove binding interactions and show remarkably high affinity for poly(dA).poly(dT) sequences. Upon photoactivation, they cleave DNA catalytically and selectively at guanine (G) sites in duplex DNA exclusively through cosensitization mechanism with a preference for 5'-G over 3'-G. They induce unusually high specificity of cleavage at G site of the AG two base bulge sequences. Accordingly, the viologen linked acridine based molecules described herein are extremely useful as probes for DNA structures and catalytic photoactivated DNA cleaving agents in biological applications.

12 Claims, 11 Drawing Sheets

Decay at 395 nm

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 1
cgtggacatt gcacggtac                                                       19

<210> SEQ ID NO 2
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 2
gtaccgtgca atgtccacg                                                       19

<210> SEQ ID NO 3
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 3
cactggcttt tcggtgcat                                                       19

<210> SEQ ID NO 4
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 4
atgcaccgaa aagccagtg                                                       19

<210> SEQ ID NO 5
<211> LENGTH: 21
```

```
<212> TYPE: DNA
<213> ORGANISM: Artificial Sequence
<220> FEATURE:
<223> OTHER INFORMATION: synthetic oligonucleotide

<400> SEQUENCE: 5
cactggcttc cttcggtgca t                                    21

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 6
cactggctta gttcggtgca t                                    21
```

VIOLOGEN LINKED ACRIDINE BASED MOLECULE AND PROCESS FOR THE PREPARATION THEREOF

FIELD OF THE INVENTION

The present invention relates to viologen linked acridine based molecule of the general formula 1 (1a, 1b, 1c, and 1d)

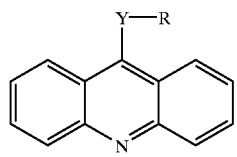

1a. wherein
  Y=—(CH$_2$)$_n$—; n=1–11
  R=—MV$^{2+}$—(CH$_2$)$_m$—CH$_3$ 2X$^\ominus$ or -Pyr$^{2+}$—(CH$_2$)$_m$—CH$_3$ 2X$^\ominus$; m=1–13

1b. wherein
  Y=—(CH$_2$)$_n$—; n=1–11
  R=—MV$^{2+}$—(CH$_2$)$_m$-Acr 2X$^\downarrow$ or -Pyr$^{2+}$-(CH$_2$)$_m$-Acr 2X$^\ominus$; m=1–11

1c. wherein
  Y=ortho or para tolyl
  R=MV$^{2+}$—(CH$_2$)$_m$—CH$_3$ 2X$^\ominus$ or -Pyr$^{2-}$-(CH$_2$)$_m$—CH$_3$ 2X$^\ominus$; m=1–13

1d. wherein
  Y=—(CH$_2$)$_n$—; n=1–10
  R=—Acr$^+$-R$^1$ X$^\ominus$/2X wherein
  N in the arcridine main ring is also quaternised by alkyl group
  R$^1$=—(CH$_2$)$_m$—CH$_3$ and —(CH$_2$)$_m$—C$_6$H$_4$—(CH$_2$)$_m$—CH$_3$ (para), m=0–13,
and wherein Formula 1

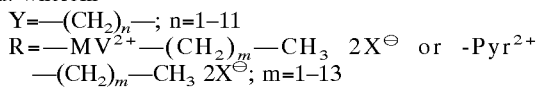

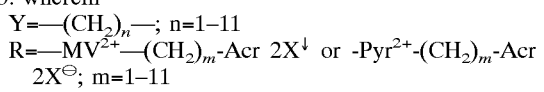

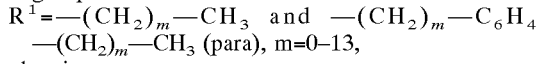

and/or pharmaceutically acceptable derivative thereof, useful as phototherapeutical and catalytic photoactivated DNA cleaving agents. The present invention also relates to a process for the preparation of the novel molecule of formula 1. The novel molecules of the invention are useful for the stabilization of DNA including duplex, triplex and quadruplex structures through intercalation and/or bisintercalation and groove binding interactions. The novel molecules of the invention are also for the catalytic photoactivated cleavage of DNA purely through cosensitization with selectivity at guanine (G) sites in duplex and AG two base bulge containing sequences.

The present invention also relates to a series of bifunctional molecules of the general formula 1 (1a, 1b, and 1c) and derivatives thereof, are also useful as photocatalysts for the oxidation of water to generate hydrogen in industrial applications.

BACKGROUND OF THE INVENTION

Design of functional molecules that bind selectively to nucleic acids (DNA or RNA) and are capable of cleaving duplex or single stranded nucleic acids is an active area of research that has important biochemical and biomedical applications. Some of these effective agents have been extremely useful in the treatment of various diseases and also as probes for understanding DNA structures and DNA-protein interactions. While natural restriction enzymes have been very useful in many of these applications, their large size and/or limited range of sequence recognition capabilities prevent their general use. Hence, synthetic functional molecules that cause site-selective or sequence specific modifications of DNA and offer a clean and efficient way of cutting DNA at sites that are not recognized by conventional restriction enzymes are highly required.

In this context, a large number of synthetic ligands have been developed, which have it ability to recognize and bind to specific sequences or structural domains in DNA and exhibit nucleolytic activity under physiological conditions (chemical nucleases) or upon photoactivation (photonucleases). Some of these include, 1,10-phenanthroline-copper, ferrous-EDTA, bleomycin, enediyene antibiotics and anthraquinones. For examples, references may be made to U.S. Pat. No. 5,985,557; No. 6,090,543; No. 5,739,022; No. 5,556,949; No. 5,552,278; No. 5,504,075; No. 4,942,227; Nielsen, P. E. *J. Mol. Recog.* 1990, 3, 1; Papavassiliou, A. G. *Biochem. J.* 1995, 305, 345; Sigman, D. S.; Graham, D. R.; D'Aurora, V.; Stern, A. M. *J. Biol. Chem.* 1979, 254, 12269; Pope, L. E.; Sigman, D. S. *Proc. Natl. Acad. Sci. USA.* 1984, 81, 3; Tullius, T. D.; Dombroski, B. A. *Proc. Natl. Acad. Sci. USA.* 1986, 83, 5469; Hertzberg, R. P.; Dervan, P. B. *J. Am. Chem. Soc.* 1982, 104, 313; Hecht, S. M.; *Bleomycin: Chemical, Biochemical and Biological aspects,* Ed., Springer Verlag: New York, 1979; Sausville, E. A.; Peisach, J.; Horwitz, S. B. *Biochemistty,* 1978, 17, 2740. However, synthetic ligands that are versatile and mimic the conventional restriction enzymes are yet to be developed.

Of the several classes of DNA cleaving systems reported, the photoactivated cleaving agents have been found to posses significant practical advantages over the reagents that cleave DNA under thermal conditions. An interesting aspect of the photoactivated DNA cleaving agent is that it allows the reaction to be controlled spatially and temporally by combining all of the components of the reaction mixture before the irradiation. Excitation of the reaction mixture with an appropriate light source initiates the reaction, which continues until the light is shut off The ability to control light, in both spatial and temporal sense would be advantageous for applications ranging from the time resolved probing of various biochemical processes such as transcription and translation to genomic analysis and therapeutic agents. For selected examples, reference may be made to U.S. Pat. No. 5,994,410; No. 5,734,032; No. 5,650,399; No. 5,607,924; No. 6,087,493; No. 6,057,096; 5,767,288: No. 5,439, 794; Armitage, B. *Chem. Rev.* 1998, 98, 1171 and references sited therein; Kochevar, I. E.; Dunn, D. A. *Bioorg. Photochem.* 1990, 1, 273 and references sited therein; Paillous, N.; Vicendo, P. *J. Photochem. Photobiol. B* 1993, 20, 203; Nielsen, P. E.; Jeppesen, C.; Buchardt, O. *FEBS lett.* 1988, 235, 122; Chow, C. S.; Barton, J. K. *Methods Enzymol.* 1992, 212, 219; Chang, C. -H.; Meares, C. F. *Biochemistry* 1982, 21, 6332; Riordan, C. G.; Wei, P. *J. Am. Chem. Soc.* 1994, 116, 2189; Thorp, H. H. *Angew. Chem., Int. Ed. Eng.* 1991, 30, 1517; Armitage, B.; Yu, C.; Devadoss, C.; Schuster, G. B. *J. Am. Chem. Soc.* 1994, 116, 9847; Adam, W.; Cadet, J.; Dall'Acqua, F.; Epe, B.; Ramaiah, D.; Saha-Moller, C. R. *Angew. Chem. Int. Ed. Engl.* 1995, 34, 107; Uesawa, Y.; Kuwahara, J.; Sugiura, Y. *Biochem. Biophys. Res. Commun.* 1989, 164, 903; Ito, K.; Inoue, S.; Yamamoto, K.; Kawanishi, S. *J. Biol. Chem.* 1993, 268, 13221; Saito, I.; Takayama, M.; Matsuura, T.; Matsugo, S.; Kawanishi, S. *J. Am. Chem. Soc.* 1990, 112, 883; Sako, M.; Nagai, K.; Maki, Y. *J. Chem. Soc. Chem. Commun.* 1993, 750.

These photoactivated cleaving agents found to cleave DNA (i) by generation of diffusible (singlet oxygen) and non-diffusible (hydroxyl radicals) reactive intermediates, (ii) hydrogen atom abstraction and (iii) electron transfer. Most of the systems reported so far, initiate photocleavage by more than one mechanism. Though the damage induced by all these mechanisms lead to the initial modification of either sugar or nucleobase, which then results in phosphodiester cleavage, serious efforts are in progress to develop reagents which cleave DNA purely by one mechanism and also to target these cleaving agents to specific sequences or domains in DNA. References may be made to Cadet, J.; Teoule, R. *Photochem. Photobiol.* 1978, 28, 661; Croke, D. T.; Perrouault, L.; Sari, M. A.; Battioni, J. P.; Mansuy, D.; Magda, D.; Wright, M. M.; Miller, R. A.; Sessler, J. L.; Sansom, P. L. *J. Am. Chem. Soc.* 1995, 117, 3629; Theodorakis, E.; Wilcoxen, K. M. *Chem. Commun.* 1996, 1927; Suenaga, H.; Nakashima, K.; Hamachi, I.; Shinkai, S. *Tetrahedron Lett.* 1997, 38, 2479; Cullis, P. M.; Malone, M. E.; Merson-Davies, L. A. *J. Am. Chem. Soc.* 1996, 118, 2775; Sies, H.; Schulz, W. A.; Steenken, S. *J. Photochem. Photobiol. B* 1996, 32, 97; Saito, I.; Takayama, M.; Sugiyama, H.; Nakamura, T. In *DNA and RNA Cleavers and Chemotherapy of Cancer and ViraL Diseases;* Meunier, B., Ed.; Kluwer: Netherlands, 1996, pp 163–176.

Recently, there has been growing interest in designing molecules, which cleave DNA effectively through photoinduced electron transfer mechanism involving purely by the oxidation of nucleobases. A unique feature of this mechanism is that one can have reasonable control over the cleavage. It has been observed that DNA cleavage by this mechanism occurs at guanine (G), since guanine is the most easily oxidizable base of the nucleic acids because of its low ionization potential. A large number of organic as well as inorganic systems have been reported which cause DNA cleavage by photoinduced electron transfer mechanism. However, most of these reagents were found to be less efficient with the cleavage efficiency in the order of $10^{-8}$. References may be made to Sevilla, M. D., D'Arcy, J. B.; Morehouse, K. M.; Englehardt, M. L. *Photochem. Pholobiol.* 1979, 29, 37; Blau, W.; Croke, D. T.; Kelly, J. M.; McConnel, D. J.; OhUigin, C.; Van der Putten, W. J. M. *J. Chem. Soc. Chem. Commun.* 1987, 751; Sage, E.; Le Doan, T.; Boyer, V.; Helland, D. E.; Kittler,; Hélène, C; Moustacchi, E. *J. Mol. Biol.* 1989, 209, 297; Brun, A. M., Harriman, A. *J. Am. Chem. Soc.* 1991, 113, 8153; Ly, D.; Kan, Y.; Armitage, B.; Schuster, G. B. *J. Am. Chem. Soc.* 1996, 118, 8747: Hall, D. B.; Holmlin, R. E.; Barton, J. K. *Nature* 1996, 382, 731; Gasper, S. M.; Schuster, G. B. *J. Am. Chem. Soc.* 1997, 119, 12762. Therefore, efficient photoactivated DNA cleaving agents based on electron transfer mechanism are highly desired for biological applications.

In the case of the photoactivated DNA cleaving agents by electron transfer mechanism, the efficiency of the reaction depends on the reduction potential of the cleaving agent, excited state energy and the oxidation potential of the ground state base, in addition to other conditions. For an efficient reaction to occur, the rate of the forward electron transfer from the donor to an acceptor must be greater than the back electron transfer process. Therefore, the inefficiency associated with the photoactivated DNA cleaving agents can be attributed to the existence of an efficient back electron transfer between the resultant oxidized base and the reduced sensitizer. To overcome the drawback of the back electron transfer process associated with such systems, a few examples based on cosensitization mechanism have been developed (Dunn, D. A.; Lin, V. H.; Kochevar, I. E. *Biochemistry* 1992, 31, 11620; Atherton, S. J.; Beaumont, P. C. *J. Phys. Chem.* 1987, 91, 3993; Fromherz, P.; Rieger, B. *J. Am. Chem. Soc.* 1986, 108, 5361). These systems consists of a sensitizer, which is also an intercalator, transfers an electron upon photoactivation to a cosensitizer (electron acceptor), bound on the surface of DNA. The photosensitization involving the cosensitizer that bound far away from the sensitizer is expected to inhibit the back electron transfer and thereby increase the DNA cleavage. However, in reality, only marginal improvement in DNA cleavage efficiency (in the order of $10^{-7}$) was observed in these systems owing to the complications with respect to the concentration, distance and DNA binding affinities of the sensitizer and cosensitizers.

Therefore, development of small compounds which are, soluble in aqueous medium, overcome the inefficiency due to the back electron transfer, undergo strong binding interactions with DNA, selective and effective in inducing DNA cleavage purely through electron transfer mechanism are highly desired for biological applications including clean and efficient way of cutting DNA at sites that are not recognized by the conventional restriction enzymes.

It is an objective of the present investigation to provide functional molecules which bind strongly and selectively with DNA and act as selective and effective photoactivated DNA cleaving agents which function purely through cosensitization mechanism.

OBJECTS OF THE INVENTION

The main objective of the present invention is to provide novel bifunctional molecules based on viologen linked acridines or derivatives thereof, which can be used as phototherapeutical and catalytic photoactivated DNA cleaving agents.

Another objective of the present invention is to provide bifunctional molecules based on viologen linked acridines or derivatives thereof, which can act as probes for various DNA structures (single strand, duplex, triplex and quadruplex) of biological significance and with high selectivity.

Yet another objective of the present invention is to provide bifunctional molecules based on viologen linked acridines or derivatives thereof, which can act as catalytic photoactivated DNA cleaving agents of duplex and base bulges containing DNA, purely through cosensitization mechanism.

Still another objective of the present invention is to provide bifunctional molecules based on viologen linked acridines or derivatives thereof, which can act as photocatalysts for the oxidation of water in industrial applications.

Accordingly the present invention relates to viologen linked acridine based molecule of the general formula 1 (1a, 1b, 1c, and 1d)—below

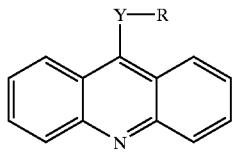

1a. wherein
Y=—(CH$_2$)$_n$—; n=1–11
R=—MV$^{2+}$—(CH$_2$)$_m$—CH$_3$ 2X$^{\ominus}$ or -Pyr$^{2+}$—(CH$_2$)$_m$—CH$_3$ 2X$^{\ominus}$; m=1–13

1b. wherein
Y=—(CH$_2$)$_n$—; n=1–11
R=—MV$^{2+}$—(CH$_2$)$_m$Acr 2X$^{\ominus}$ or -Pyr$^{2+}$—(CH$_2$)$_m$-Acr 2X$^{\ominus}$; m=1–11

1c. wherein
Y=ortho or para tolyl
R=—MV$^{2+}$—(CH$_2$)$_m$—CH$_3$ 2X$^{\ominus}$ or -Pyr$^{2+}$(CH$_2$)$_m$—CH$_3$ 2X$^{\ominus}$; m=1–13

1d. wherein
Y=—(CH$_2$)$_n$—; n=1–10
R=-Acr$^+$—R$^1$ X$^{\ominus}$/2X wherein N in the acridine main ring is also quaternised by alkyl group
R$^1$=—(CH$_2$)$_m$—CH$_3$ and —(CH$_2$)$_m$—C$_6$H$_4$—(CH$_2$)$_m$—CH$_3$ (para), m=0–13,
and wherein Formula 1

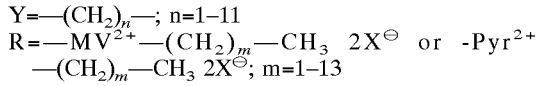
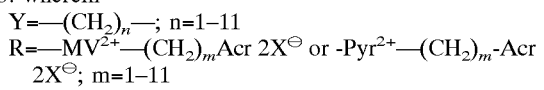
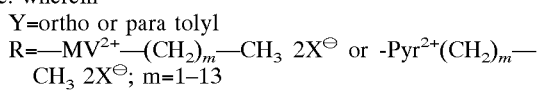

The present invention also relates to a process for the preparation of the novel bifunctional molecule based on viologen linked acridines, bisacridines and acridinium salts of the general formula 1 (1a, 1b, 1c and 1d) above, said process comprising forming a solution of ω-(acridin-9-yl)-α-bromoalkanes and/or 1-alkyl-4,4'-bipyridinium bromides in dry acetonitrile in the ratio of 1:1, stirring the solution at a temperature in the range of 20–50° C. for a time period in the range between 8–24 h to obtain a precipitate, filtering, and washing the precipitate with dry acetonitrile and dichloromethane to remove any unreacted starting materials, purifying the solid so obtained to give obtain compound of formula 1 (1a, 1b, 1c and 1d).

In one embodiment of the invention, the compounds of formula 1 are preferably recrystallized from a mixture (1:4) of methanol and acetonitrile.

Yet another embodiment of the present invention relates to bifunctional molecules of the general formula 1 (1a, 1b, 1c and 1d) and pharmaceutically acceptable derivatives thereof for the photocatalytic cleavage of DNA at G sites of duplex and AG two base bulges containing DNA purely through cosensitization mechanism.

In another embodiment of the invention, bifunctional molecules of the general formula 1 (1a, 1b, 1c and 1d) and pharmaceutically acceptable derivatives thereof are used as DNA targeted diagnostic or phototherapeutic agents.

In another embodiment of the present invention the bifunctional molecules of the invention are used for the stabilization of DNA including duplex, triplex and quadruplex structures through intercalation, bisintercalation and groove binding.

Yet another embodiment of the present invention is the use of the bifunctional molecules of general formula 1 (1a, 1b, 1c and 1d) for the photocatalytic cleavage of DNA with selectivity at G sites of duplex and AG two base bulges and as probes for these structures.

Still another embodiment of the present invention is that the bifunctional molecules and derivatives thereof of the general formula 1 (1a, 1b, and 1c) are used as photocatalysts for the oxidation of water in industrial applications.

BRIEF DESCRIPTION OF THE ACCOMPANYING DRAWINGS

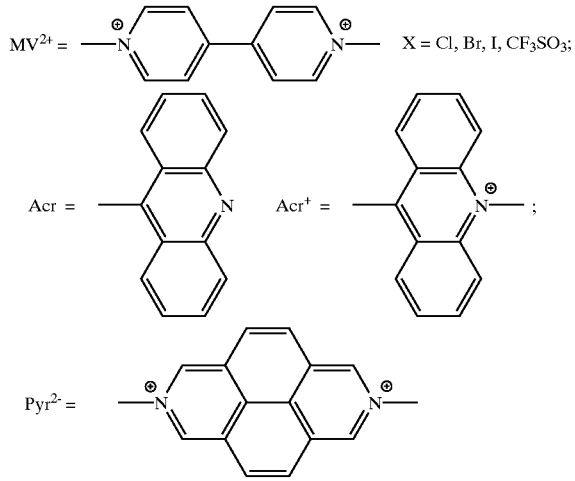

(10 μM) induced by compound of formula 1a wherein n=1, R=—MV$^{2+}$—(CH$_2$)$_3$—CH$_3$ and X=Br and formula 1b wherein n=1, R=—MV$^{2+}$—CH$_2$—Acr and X=Br with piperidine treatment (90° C., 30 min). Lane 1: DNA (3) (control). Lane 2: DNA (3) and 50 μM of compound of formula 1a wherein n=1, R=—MV$^{2+}$—(CH$_2$)$_3$—CH$_3$ and X=Br a Lane 3: DNA (3) and 50 μM of compound of formula 1b wherein n=1, R=—MV$^{2+}$—CH$_2$—Acr and X=Br. Lane 4: DNA (5) and 50 μM of compound of formula 1a wherein n=1, R=MV$^{2+}$—(CH$_2$)$_3$—CH$_3$ and X=Br. Lane 5: DNA (5) and 50 μM of compound of formula 1b wherein n=1, R=—MV$^{2+}$—CH$_2$—Acr and X=Br. Lane 6: DNA (6) and 50 μM of compound of formula 1a wherein n=1, R=—MV$^{2+}$—(CH$_2$)$_3$—CH$_3$ and X=Br. Lane 7: DNA (6) and 50 μM of compound of formula 1b wherein n=1, R=MV$^{2+}$—CH$_2$—Acr and X=Br. The Maxam-Gilbert sequencing lanes are marked with A/G and T.

Figure 8:
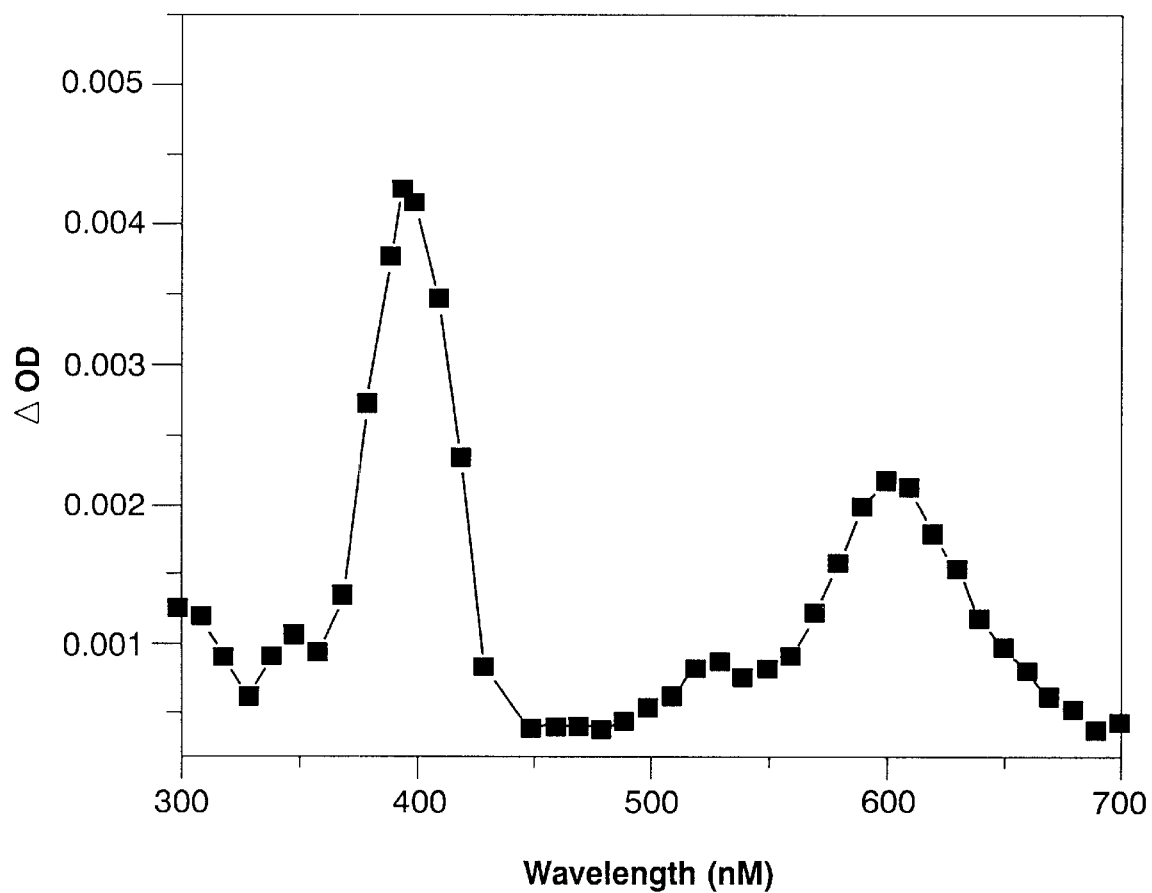
Figure 8A:
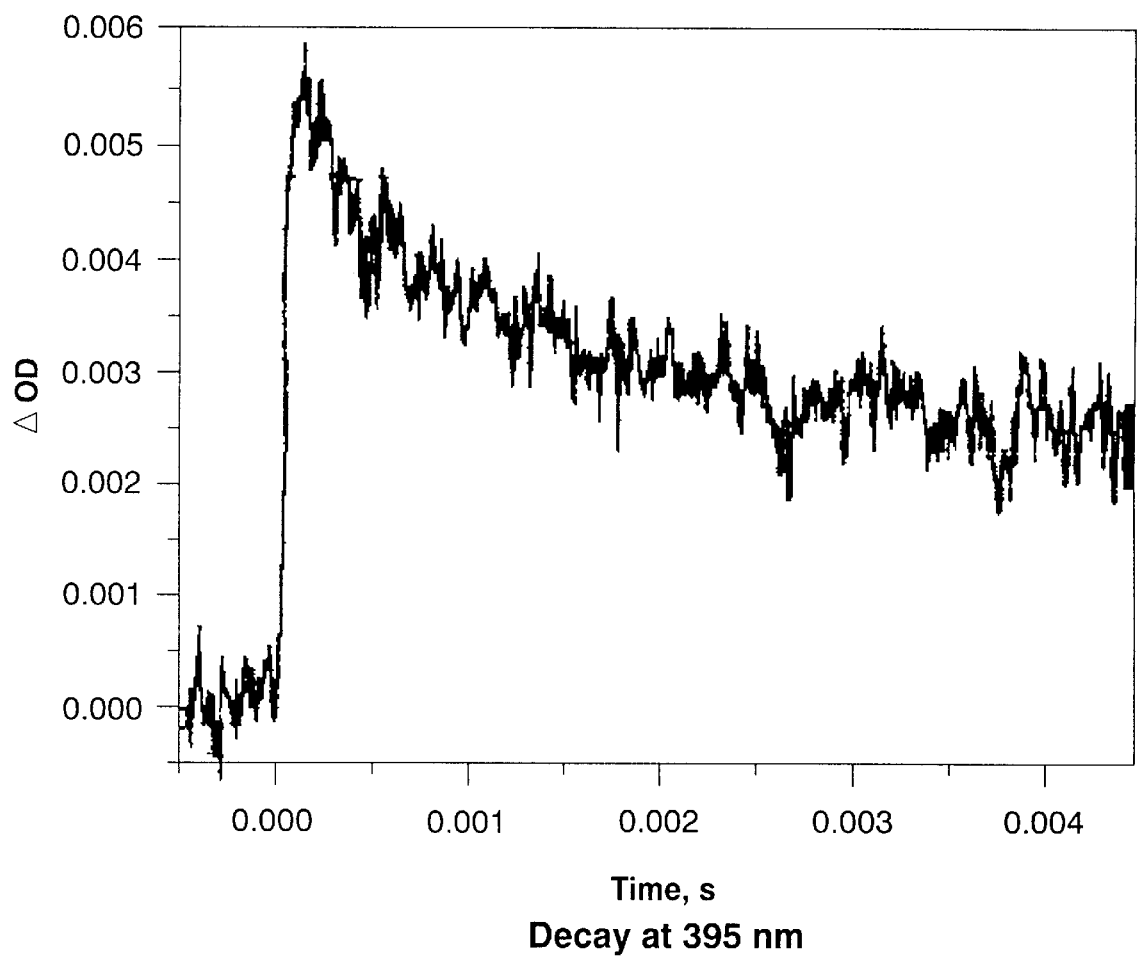

FIG. 8 shows the formation of reduced methyl viologen upon irradiation of compound of formula 1a wherein n=11, R=—MV$^{2+}$—(CH$_2$)$_3$—CH$_3$ and X=Br in presence of DNA (sacrificial electron donor), demonstrating the catalytic properties of viologen linked acridines.

DETAILED DESCRIPTION OF THE INVENTION

In the present invention, the novel bifunctional molecules incorporate a DNA intercalator and cosensitizer linked through rigid to flexible spacer groups. The intercalator such as acridine moiety is capable of absorption in the visible region and acting as an electron-donor (sensitizer) in the excited state. The cosensitizer, methyl viologen moiety, on the other hand, is a very good electron acceptor and is capable of undergoing groove-binding interactions with DNA. The rigid to flexible spacer groups play a major role in controlling the rate of electron transfer in these systems through the alteration of distance and relative orientation between the intercalator and cosensitizer.

In the present invention, a series of novel viologen linked acridine, bisacridine and bisacridinium salts of the general formula 1 (1a, 1b, 1c and 1d) have been synthesised, having flexible to rigid spacer groups and their photophysical properties examined under different conditions. Further the DNA binding and DNA stabilization properties of these molecules have been examined employing calf thymus DNA and synthetic oligonucleotides. The photoactivated DNA cleaving properties were investigated and the sequence specific cleavage induced by these compounds by employing plasmid DNA, the synthetic duplex and base bulge containing DNA sequences were also analysed. Further the mechanism of their biological and catalytic activities have been evaluated.

As a result, it is observed that compounds of the general formula 1 (1a, 1b, 1c and 1d) and their derivatives thereof posses good solubility at physiological pH conditions and exhibit good absorption properties. Further protonation of the acridine ring leads to the formation of corresponding acridinium salts which show quite different and interesting photophysical and redox properties. The absorption and fluorescence studies confirm the existence of through bond and through space interactions between viologen and acridine moieties. Further, efficient quenching of fluorescence yields was observed and which indicate the mechanism of quenching is through electron transfer mechanism with rates in the order of $10^{10}$.

Interestingly, these bifunctional molecules exhibit strong binding with DNA through intercalation and or bisintercalation and groove binding interactions and with unusually high affinity for the poly(dA).poly(dT) sequence. Upon excitation, these molecules cleaved DNA very effectively and with high selectivity at guanine (G) sites and predominance of 5'-G of GG step. Moreover, these molecules are found to be very attractive for sequences containing base bulges and cleave upon photoactivation specifically at the G sites of the AG base bulge. The DNA cleavage induced by these compounds is purely through the electron transfer mechanism, where the excited acridine moiety transfers an electron to methyl viologen (MV$^{2+}$) and lead to the radical cation of acridine and radical cation of methyl viologen (MV$^+$). The radical cation of acridine once formed, can oxidize DNA base at the site of binding and ultimately resulted in efficient cleavage of DNA at the G sites, as expected. Moreover, these molecules are found to be recyclable and act as catalysts in presence of sacrificial electron donors. Therefore, the present systems are not only bifunctional with interesting photophysical properties but also recyclable and act as effective photoactivated DNA cleaving-and phototherapeutical agents and photocatalysts for the oxidation of water in industrial applications.

Table 1 shows DNA association constants of bifunctional molecules based on viologen linked acridines compound of formula 1a wherein n=1, R=—MV$^{2+}$—(CH$_2$)$_3$—CH$_3$ and X=Br and wherein n=11, R=—MV$^2$—(CH$_2$)$_3$—CH$_3$ and X=Br and bisacridine system (compound of formula 1b wherein n=1, R=—MV$^{2+}$—CH$_2$—Acr and X=Br) in buffer containing 1 mM EDTA and 2 or 100 mM NaCl.

Table 2 shows the structures of oligonucleotides used for DNA melting studies.

Table 3 shows the structures of oligonucleotides used for DNA cleaving studies.

The present invention accordingly provides a process for the preparation of bifunctional molecules represented by compound of formula 1 (1a, 1b, 1c and 1d) and derivatives thereof.

Bifunctional molecules of general formula 1 (1a, 1b, 1c and 1d) and pharmaceutically acceptable derivatives thereof are useful for the stabilization of DNA structures including duplex, triplex and quadruplex DNA. The bifunctional molecules of general formula 1 (1a, 1b, 1c and 1d) and pharmaceutically acceptable derivatives thereof are also useful for the photocatalytic cleavage of DNA at G sites of duplex and AG two base bulges containing DNA purely through cosensitization mechanism. The novel molecules of the invention and pharmaceutically acceptable derivatives thereof are useful as DNA targeted diagnostic or phototherapeutic agents. These sensitizers can be used for diagnosis or treatment of human beings or animals.

The bifunctional molecules of the invention are used for the stabilization of DNA including duplex, triplex and quadruplex structures through intercalation, bisintercalation and groove binding. The bifunctional molecules of general formula 1 (1a, 1b, 1c and 1d) can also be used for the photocatalytic cleavage of DNA with selectivity at G sites of duplex and AG two base bulges and hence can be used as probes for these structures. Bifunctional molecules and derivatives thereof of the general formula 1 (1a, 1b, and 1c) are used as photocatalysts for the oxidation of water in industrial applications.

The following examples are given by way of illustration and therefore should not be construed to limit the scope of present investigation.

Examples 1–4 represent typical synthesis of compounds of general formula 1 (1a, 1b, 1c and 1d) and Examples 5–11 represent photophysical and in vitro DNA binding and cleaving properties of bifunctional viologen linked acridine based molecules.

EXAMPLE 1

General procedure for the preparation of formulae represented by compound of formula 1a (wherein Y=—(CH$_2$)$_n$, wherein n=1–11; R=—MV$^{2+}$—(CH$_2$)$_m$—CH$_3$2X$^\ominus$ or —Pyr$^{2+}$—(CH$_2$)$_m$—CH$_3$2X$^\ominus$). A solution of ω-(acridin-9-yl)-α-bromoalkanes (1–10 mmol) and 1-alkyl-4,4'-bipyridinium bromides (1–10 mmol, which in turn were obtained in 93–98% yields by the reaction of 4,4'-bipyridine with the corresponding α-bromoalkanes in the molar ratio of 3:1.) in the ratio of 1:1 in dry acetonitrile (30–50 mL) was stirred at 20° C. for 10 h. The precipitated solid thus obtained was filtered, washed with dry acetonitrile and dichloromethane to remove any unreacted starting materials. The solid was further purified by soxhlet extraction with dichloromethane to give the compound of formula 1a in 70–95% yields. These compounds were recrystallized from a mixture (1:4) of methanol and acetonitrile.

The physiochemical properties of 1-[(acridin-9-yl)methyl]-1'-butyl-4,4'-bipyridinium dibromide (compound of formula 1a wherein n=1, R=—MV$^{2+}$—(CH$_2$)$_3$—CH$_3$ and X=Br): melting point: 260–261° C.; Molecular Weight: MS (FAB), m/z 484 (M$^+$Br$^-$); $^1$H NMR (300 MHz, DMSO-d$_6$): δ=0.91 (t, 3H), 1.26–1.33 (m, 2H), 1.89–1.94 (m, 2H), 4.66 (t, 2H), 7.11 (s, 2H), 7.77 (t, 2H), 7.97 (t, 21), 8.31 (d, 2H), 8.53 (d, 2H), 8.59 (d, 21), 8.66 (d, 2H), 9.19 (d, 2H), 9.31 (d, 2H); $^{13}$C NMR (75 MHz, DMSO-d$_6$) δ=149.78–121.41, 61.05, 55.44, 33.01, 19.10, 13.66; Nature: Pale yellow powder.

The physiochemical properties of 1-[3-(acridin-9-yl)propyl]-1'-butyl-4,4'-bipyridinium dibromide (compound of formula 1a wherein n=3, R=—MV$^{2+}$—(CH$_2$)$_3$—CH$_3$ and X=Br): melting point: 253–254° C.; Molecular Weight: MS (FAB): m/z 433 (M$^-$); $^1$H NMR (300 MHz, DMSO-d$_6$) δ=0.95 (t, 3H), 1.28–1.40 (m, 2H), 1.92–2.02 (m, 2H), 2.46–2.51 (m, 4H), 3.95 (t, 2H), 4.74 (t, 2H), 7.79 (t, 2H), 8.05 (t, 2H), 8.28 (d, 2H), 8.83–8.86 (m, 6H), 9.45 (d, 2H), 9.57 (d, 2H); $^{13}$C NMR (75 MHz, DMSO-d$_6$) δ=149.45–124.96, 61.44, 60.73, 33.21, 33.15, 24.79, 19.27, 13.80; Nature: Pale yellow powder.

The physiochemical properties of 1-[11-(acridin-9-yl)undecyl]-1'-butyl-4,4'-bipyridinium dibromide (compound of formula 1a wherein n=11, R=—MV$^{2+}$—(CH$_2$)$_3$—CH$_3$ and X=Br): melting point: 248–249° C.; Molecular Weight: MS (FAB): m/z 545 (M$^-$); $^1$H NMR (300 MHz, DMSO-d$_6$): δ=0.95 (t, 3H), 1.23–1.71 (m, 18H), 1.95–1.98 (m, 4H), 3.65 (t, 2H), 4.73 (t, 4H), 7.65 (t, 2H), 7.85 (t, 2H), 8.14 (d, 2H), 8.38 (d, 2H), 8.82 (d, 4H), 9.43 (d, 4H); $^{13}$C NM (75 Mz, DMSO-d$_6$): 148.97–124.71, 61.25, 61.04, 33.07, 31.64, 31.15, 29.68, 29.26, 29:13, 28.76, 27.13, 25.7–9, 19.15, 13.71; Nature: Pale yellow powder.

EXAMPLE 2

General procedure for the preparation of formulae represented by compound of formula 1b (wherein Y=—(CH$_2$)$_n$, wherein n=1–11; R=—MV$^{2+}$—(CH$_2$)$_m$—Acr2X$^\ominus$ or —Pyr$^2$—(CH$_2$)$_m$—Acr2X$^\ominus$). A solution of ω-(acridin-9-yl)-α-bromoalkanes (2–10 mmol) and 4,4'-bipyridine (1–5 mmol) in the ratio of 2:1 in dry acetonitrile (50–150 mL) was stirred at 35° C. for 20h. Precipitated solid was filtered and washed with dichloromethane and acetonitrile. Soxhlet extraction of the solid with dichloromethane gave compound of formula 1b in 65–90% yields.

The physiochemical properties of bis-1,1'-[(acridin-9-yl)methyl]-4,4'-bipyridinium dibromide (1b wherein n=1, R=—MV$^{2-}$—CH$_2$—Acr and X=Br): melting point: >400° C.; Molecular Weight MS (FAB): m/z 619 (M$^+$Br$^-$); $^1$H NMR (300 MHz, DMSO-d$_6$): δ=7.09 (s, 4H), 7.77–7.95 (m, 8H), 8.21–8.55 (m, 161), 9.05–9.16 (m, 8); $^{13}$C NMR (75 MHz, DMSO- d$_6$) δ=150.85–124.51, 58.52; Nature: Pale yellow powder.

The physiochemical properties of bis-1,1'-[3-(acridin-9-yl)propyl]-4,4'-bipyridinium dibromide (1b wherein n=3, R=—MV$^{2+}$—(CH$_2$)$_3$—Acr and X=Br): melting point: 223–224° C.; Molecular Weight: MS (FAB): m/z 596 (M$^+$); $^1$H NMR (300 MHz, D$_2$O): δ=2.50–2.60 (m, 4H), 3.95 (t, 4H), 4.9 (t, 4H), 7.79–7.83 (m, 6H), 8.01–8.07 (m, 8H), 8.26 (d, 2H), 8.46–8.48 (m, 4H), 8.69 (d, 2H), 8.93 (d, 2H); $^{13}$C NMR (75 MHz, DMSO-d$_6$): δ=150.82–121.86, 60.26, 32.36, 24.30; Nature: Pale yellow powder.

The physiochemical properties of bis-1,1'-[11-(acridin-9-yl)undecyl]4,4'-bipyridinium dibromide (1b wherein n=11, R=—MV$^{2+}$—(CH$_2$)$_{11}$—Acr and X=Br): melting point: 152–153° C.; Molecular Weight: MS (FAB): m/z 820 (M+); $^1$H NMR (300 MHz, DMSO-d$_6$): δ=1.22–1.94 (m, 36H), 3.63 (t, 4H), 4.64 (t, 4H), 7.65 (t, 4H), 7.85(t, 4H), 8.04 (d, 4H), 8.15 (d, 4H), 8.37 (d, 2H), 8.63 (d, 2H), 8.87 (d, 2H), 9.24 (d, 2H): $^{13}$C NMR (75 MHz, DMSO-d$_6$): δ=151.36–122.30, 60.83, 31.63, 31.07, 29.69, 29.26, 29.11, 28.75, 27.13, 25.79; Nature: Pale yellow powder.

EXAMPLE 3

Synthesis of compound of formula 1c (wherein Y=ortho or para tolyl; R=MV$^{2-}$—(CH$_2$)$_m$—CH$_3$2X$^\ominus$ or —Pyr$^{2+}$—(CH$_2$)$_m$—CH$_3$2X$^\ominus$). A solution of 9-(2-bromomethylphenyl)acridine (1–5 mmol) and 1-butyl-4,4'-bipyridinium bromide (1–5 mmol) in the ratio of 1:1 in dry acetonitrile (30–120 mL) was stirred at 50° C. for 15h. The precipitated solid thus obtained was filtered, washed with dry acetonitrile and dichloromethane to remove any unreacted starting materials. The solid was further purified by soxhlet extraction with dichloromethane to give compound of formula 1c (wherein n=1, R=—MV$^{2+}$—(CH$_2$)$_3$—CH$_3$, X=Br and acridine is at the ortho position) in 35–55% yield and the product was further purified by recrystallization from ethyl acetate. Similarly, the reaction of 9-(4-bromomethyl phenyl)acridine (1–5 mmol) and 1-butyl-4,4'-bipyridinium bromide (1–5 mmol) in the ratio of 1:1 in dry acetonitrile (30–120 mL) gave compound of formula 1c (wherein n=1, R=—MV$^{2-}$—(CH)$_3$—CH$_3$, X=Br and acridine is at the para position) in 55–70% yield and the product was further purified by recrystallization from ethyl acetate.

The physiochemical properties of 1-[(2-(acridin-9-yl)-1-methyl)phenyl]-1'-butyl-4,4'-bipyridinium dibromide (1c wherein n=1, R=—MV$^{2+}$—(CH$_2$)$_3$—CH$_3$, X=Br and acridine is at the ortho position): melting point: 224–225° C.; Molecular Weight: MS (FAB): m/z: 561 (M$^+$Br$^-$); $^1$H NMR (300 MHz, DMSO-d$_6$): δ=0.95 (t, 3H), 1.31–1.39 (m, 2H), 1.95–2.00 (m, 2H), 4.73 (t, 2H), 5.56 (s, 2H), 7.21 (d, 2H), 7.42 (t, 21), 7.5 (d, 2H), 7.75–7.89 (m, 4H), 8.20–8.23 (m, 4H), 8.41 (d, 2H), 8.55 (d, 2H), 9.4 (d, 2H); $^{13}$C NMR (75 MHz, DMSO-d$_6$): δ=148.49–124.24, 62.01, 60.64, 32.67, 18.78, 13.35; Nature: Yellow powder.

The physiochemical properties of 1-[(4-(acridin-9-yl)-1-methyl)phenyl]-1'-butyl-4,4'-bipyridinium dibromide (1c wherein n=1, R=—MV$^{2+}$—(CH$_2$)$_3$—CH$_3$, X=Br and acridine is at the para position): melting point: 268–269° C.; Molecular Weight: MS (FAB): m/z 561 (M$^+$Br$^-$); $^1$H NMR (300 MHz, DMSO-d$_6$): δ=0.94 (t, 3H), 1.31–1.38 (m, 2H), 1.90–1.95 (m, 2H), 4.72 (t, 2H), 6.18 (s, 2H), 7.57–7.65 (m, 6H), 7.88–7.92 (m, 4H), 8.24 (d, 2H), 8.86 (d, 2H), 8.88 (d, 2H), 9.43 (d, 2H), 9.69 (d, 2H); $^{13}$C NMR (75 MHz, DMSO-d$_6$): δ=149.23–124.22, 62.86, 60.63, 32.70, 18.76, 13.32; Nature: Yellow powder.

EXAMPLE 4

General procedure for the preparation of formulae represented by compound of formula 1d (wherein Y=—(CH$_2$)$_n$, n=1–10; R=-Acr$^+$-R$^1$ X$^\ominus$/2X$^\ominus$, wherein N in the acridine main ring is also quaternised by alkyl group. R$^1$=—(CH$_2$)$_m$—CH$_3$ and —(CH$_2$)$_m$—C$_6$H$_4$—(CH$_2$)$_m$—CH$_3$ (para), m=0–13). A solution of α,ω-bis(9-acridinyl)alkane (1–5 mmol) and alkyl halide (3–15 mmol) in the ratio of 1:3 in dry acetonitrile (30–150 mL) was refluxed for 8–24 h. The precipitated solid was filtered and washed with dry acetonitrile and dichloromethane in small portions to remove unreacted starting materials. The solid was further purified by recrystallization from a mixture (1:4) of ethyl acetate and acetonitrile to give compound of formula 1d in 65–95% yields.

The physiochemical properties of compound of formula 1d (wherein n=5, R=—Acr$^-$—CH$_3$ and X=I): melting point: 222–223° C.; Molecular Weight: MS (FAB): m/z 561 (M$^+$Br$^-$) $^1$H NMR (300 MHz, DMSO-d$_6$): δ=1.88 (m, 6H), 3.99 (t, 4H), 4.82 (s, 6H), 8.01 (t. 4H), 8.35 (t, 4H), 8.78 (d, 4H), 8.87 (d, 4H); $^-$C NMR (75 MHz, DMSO-d$_6$): δ=164.38–20.01, 32.60, 32.22, 30.19, 29.37; Nature: Yellow powder.

The physiochemical properties of compound of formula 1d (wherein n=10, R=—Acr$^+$—CH$_3$ and X=I): melting point: 230–232° C.; $^1$H NMR (300 MHz, DMSO-d$_6$): δ=1.26–1.74 (m, 16H), 3.97 (t, 4H), 4.82 (s, 6H), 8.03 (t, 4H), 8.43 (t, 4H), 8.77 (d, 4H), 8.9 (d, 4H); $^{13}$C NMR (75 MHz, DMSO-d$_6$): δ=164.65–120.03, 33.75, 33.05, 29.94, 29.44, 29.32, 24.97; Nature: Yellow powder.

EXAMPLE 5

DNA binding efficiency. DNA binding affinities of acridine-viologen bifunctional molecules represented by compound of formula 1a and 1d were analyzed using calf thymus DNA, in NaCl buffer at different salt concentrations (2 mM and 100 mM). Test solutions containing different concentrations of calf thymus DNA in NaCl buffer were incubated at room temperature for one hour to complete the complexation and were analyzed using absorption and fluorescence techniques. Strong hypochromicity in absorption and effective quenching of fluorescence emission yields of viologen linked acridines were observed in presence of DNA. The binding constants of viologen linked acridines with DNA were determined according to the reported procedures. References may be made to Peacocke, A. R.; Skerrett, J. N. H. *Trans. Faraday Soc.* 1956, 52, 261; McGhee, J. D.; von Hippel, P. H. *J. Mol. Biol.* 1974, 86, 469; Scatchard, G. Ann. N.Y. Acad. Sci 1949, 51, 660; Adam, W.; Cadet, J.; Dall'Acqua, F.; Epe, B.; Ramaiah, D.; Saha-Moller, C. R. *Angew. Chem. Int. Ed. Engl.* 1995, 34, 107). These molecules exhibited appreciable binding affinity (in the order of 10$^6$) for calf thymus DNA and were found to be one order less at higher salt concentration (Table 1). Further fluorescence lifetimes of these compounds were also examined in presence and absence of DNA.

TABLE 1

| Compound | Ionic strength | K (M$^{-1}$) |
|---|---|---|
| 1a wherein n = 1; R = -MV$^{2+}$—(CH$_2$)$_3$—CH$_3$; X = Br | 2 mM NaCl | 9.24 × 10$^5$ |
| | 100 mM NaCl | 1.01 × 10$^5$ |
| 1a wherein n = 11; R = -MV$^{2+}$—(CH$_2$)$_3$—CH$_3$; X = Br | 2 mM NaCl | 5.24 × 10$^6$ |
| | 100 mM NaCl | 1.64 × 10$^5$ |
| 1b wherein n = 1; R = -MV$^{2+}$—CH$_2$-Acr; X = Br | 2 mM NaCl | 1.30 × 10$^6$ |
| | 100 mM NaCl | 3.90 × 10$^5$ |

These results indicate that the planar acridine ring can intercalate between the base pairs of calf thymus DNA in a position perpendicular to the helix axis. At the same time, the viologen moiety interacts electrostatically with the phosphate backbone of the DNA. The strong dependence of the binding constants on ionic strength of the buffer medium is a strong indication that these systems interact with DNA through intercalation as well as by groove binding, indicating their bifunctional in character.

EXAMPLE 6

Figure 1:
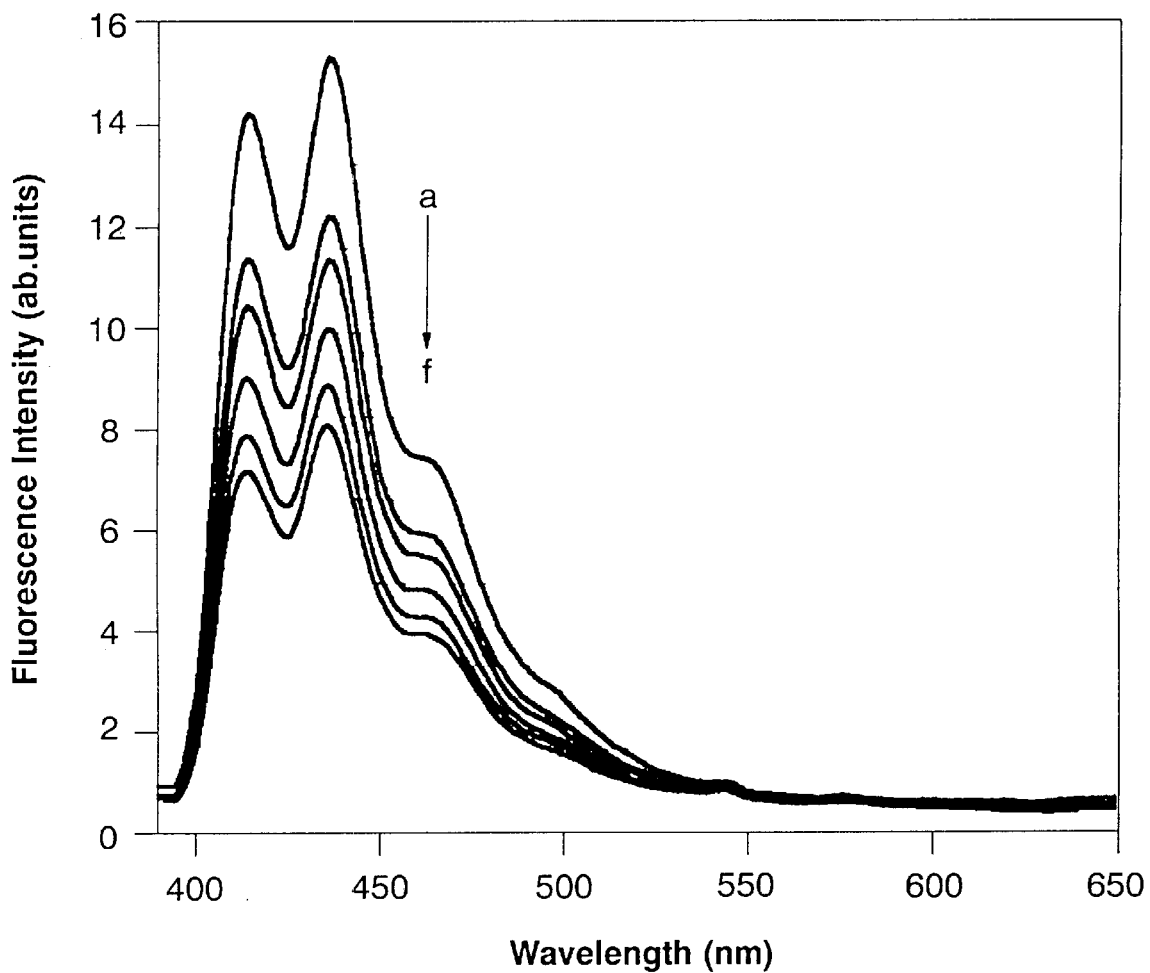
FIG. 1 shows the fluorescence enhancement of the compound of formula 1a (wherein n=1, R=—MV$^2$—(CH$_2$)$_3$—CH$_3$ and X=Br) in presence of various concentrations of poly(dA).poly(dT).
Figure 1A:
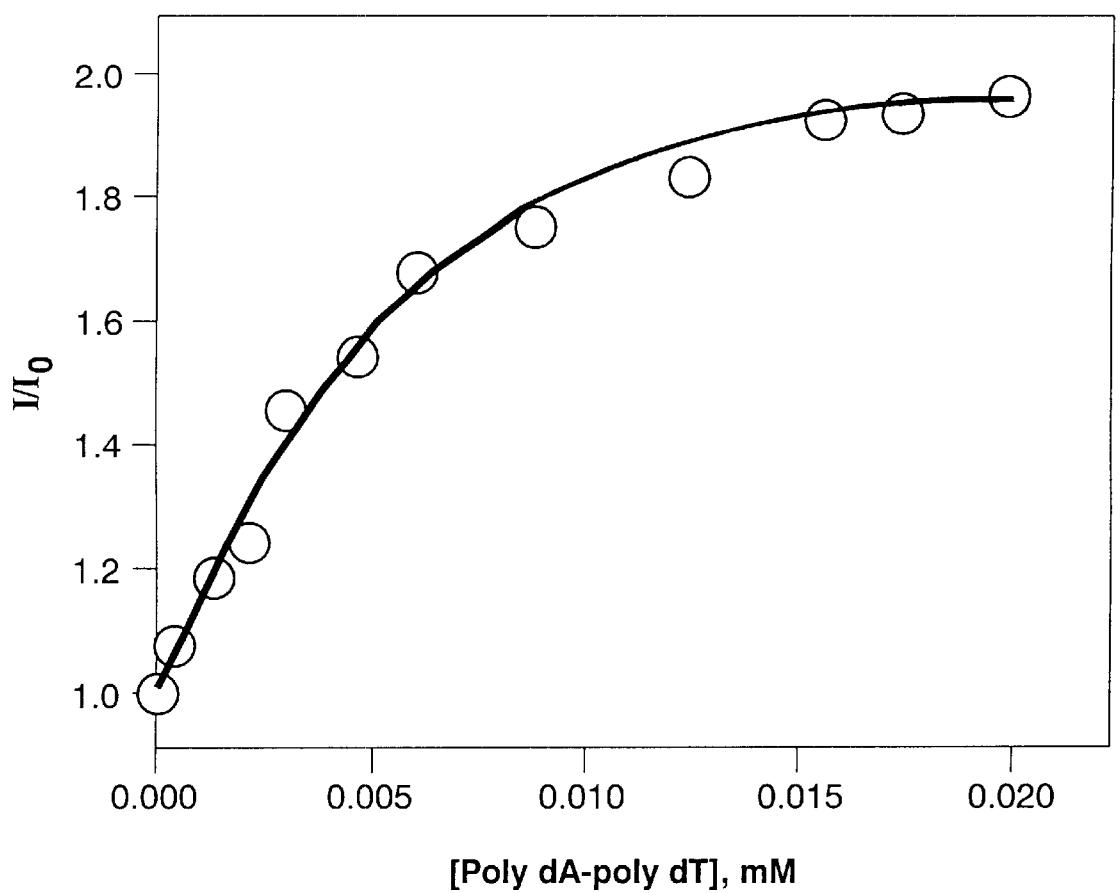

Demonstration of special affinity for poly(dA).poly(dT) sequence. In order to have a better understanding on the binding site of acridine chromophore in viologen linked acridines in DNA, the absorption and fluorescence properties of these molecules were examined in presence of various polynucleotides. The gradual addition of poly(dA).poly(dT) to the buffered solutions of viologen linked acridines led to a gradual decrease in absorption intensity with a strong enhancement in their fluorescence emission yields (FIG. 1). However, no significant changes were observed when a solution of poly(dG).poly(dC) was added. These results indicate the fact that the viologen linked acridines examined herein posses special affinity for A.T sequence and hence can have potential applications as probes for the detection of such sequences in DNA.

EXAMPLE 7

Figure 2:
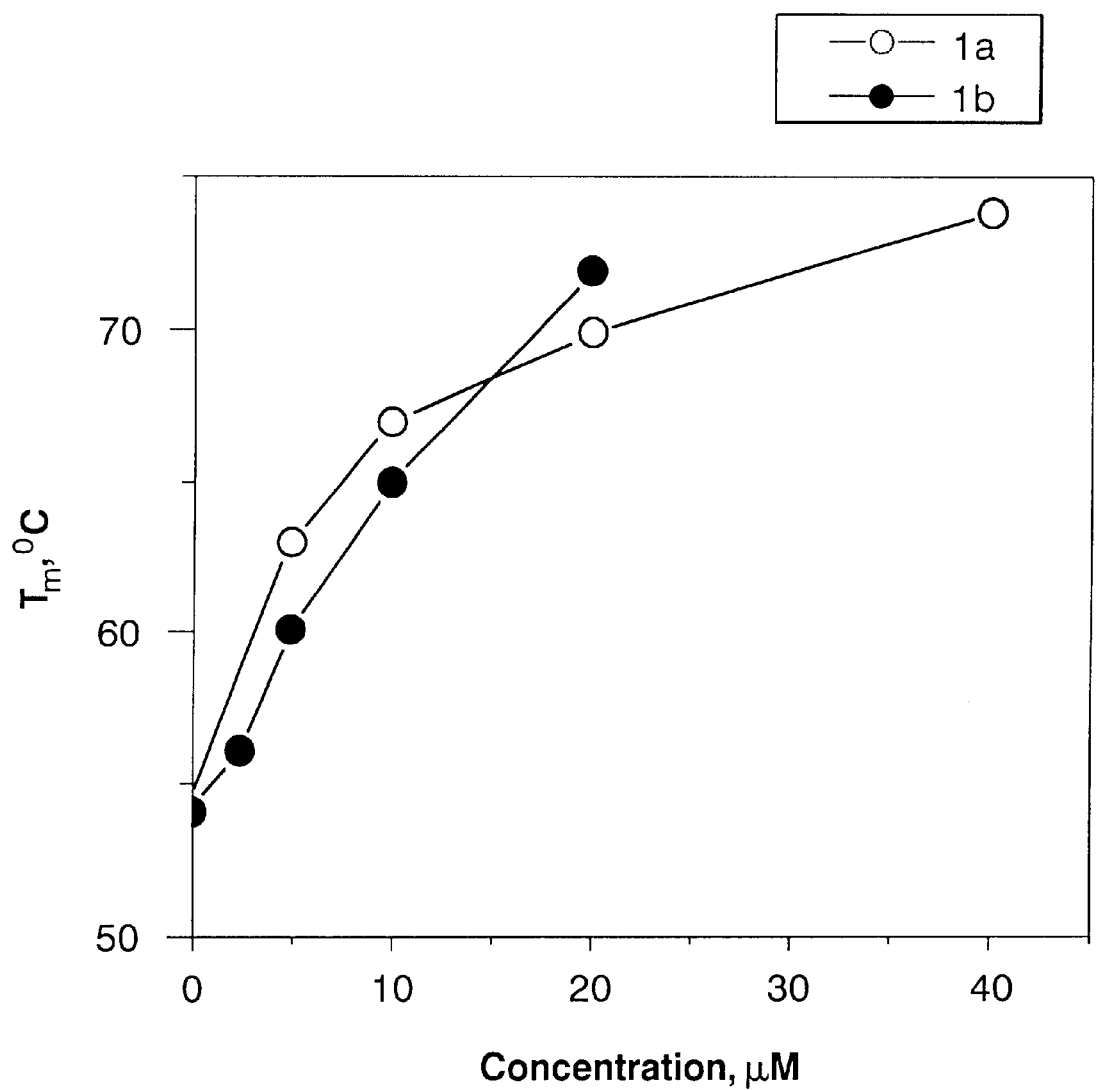
FIG. 2 shows the effect on thermal denaturation temperature of DNA duplex by various concentrations of compound of formula 1a wherein n=1, R=—MV$^{2-}$—(CH$_2$)$_3$—CH$_3$ and X=Br and formula 1b wherein n=1, R=—MV$^{2+}$—CH$_2$—Acr and X=Br.

Enhancement in thermal stability of DNA. Intercalation of small ligands into DNA duplex is known to increase the DNA melting temperature (T$_m$), i.e. the temperature at which the double helix denatures into single stranded DNA (Gasparro, F. P. *Psoralen DNA photobiology,* CRC Press Inc.; Boca Raton, Fla., 1988; Patel, D. J.; Cannel, *J. Proc. Natl. Acad. Sci. USA* 1976, 73, 674). To examine the effect of the present systems on the thermal denaturation of DNA, experiments were carried out employing calf thymus DNA and synthetic oligonucleotides listed in Table 2. In 10 mM phosphate buffer, both compound of formula 1a and 1b (wherein Y—(CH$_2$)$_n$, wherein n=1–11; R=—MV$^{2+}$—(CH$_2$)$_m$—CH$_3$2X$^\ominus$ or —Pyr$^{2+}$—(CH$_2$)$_m$—CH$_3$2X$^\ominus$ and wherein Y=—(CH$_2$)$_n$, wherein n=1–11; R=—MV$^{2+}$—(CH$_2$)$_m$—Acr2X$^\ominus$ or —Pyr$^{2+}$—(CH$_2$)$_m$—Acr2X$^\ominus$ respectively) were found to stabilize the DNA and the extent of stabilization increases with the increasing in concentration of viologen linked acridines as shown in FIG. 2. At all concentrations of the ligand only one transition temperature was observed, in each case, thereby indicating that only one type of binding with DNA is responsible for such behavior. The extent of stabilization was found to be nearly 20° C. in the case of at 40 μM of compound of formula 1a (wherein Y=—(CH$_2$)$_n$, wherein n=1–11; R=—MV$^{2+}$—(CH$_2$)$_m$—CH$_3$2X$^\ominus$ or —Pyr$^{2+}$—(CH$_2$)$_m$—CH$_3$2X$^\ominus$), whereas 20 μM of compound of formula 1b (wherein Y=—(CH$_2$)$_n$, wherein n=1–11; R=—MV$^{2+}$—(CH$_2$)$_m$—Acr2X$^\ominus$ or —Pyr$^{2+}$—(CH$_2$)$_m$—Acr2X$^\ominus$)showed nearly 18° C. stability.

TABLE 2

DNA sequence

| | |
|---|---|
| SEQ ID NO: 1 | 5'-CGT GGA CAT TGC ACG GTA C-3' |
| SEQ ID NO: DNA(2) | 5'-GTA CCG TGC AAT GTC CAC G-3' |

Figure 3:
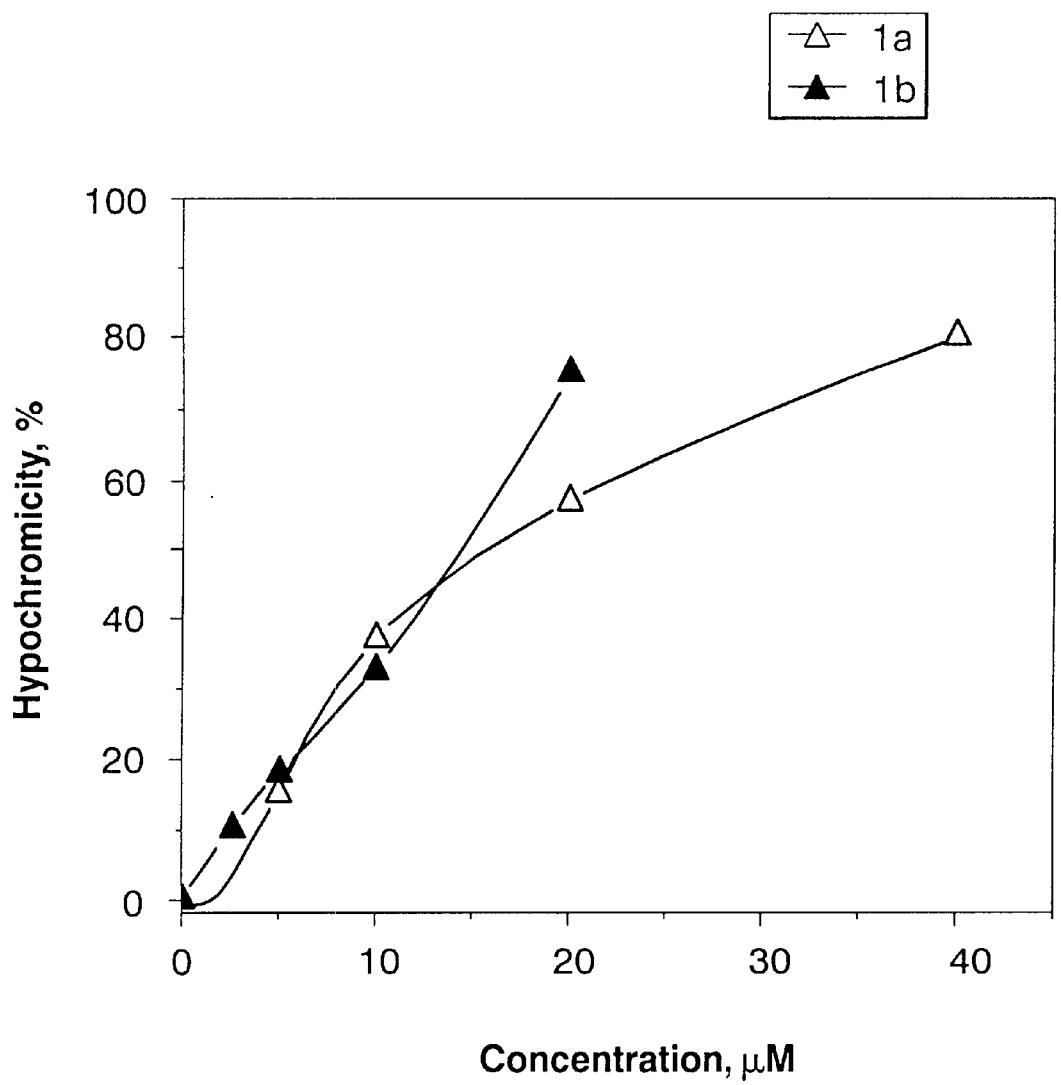
FIG. 3 shows the hypochromocity observed in DNA duplex absorption in presence of various concentrations of compound of formula 1a wherein n=1, R=MV$^{2-}$—(CH$_2$)$_3$—CH$_3$ and X=Br and formula 1b wherein n=1, R=—MV$^{2+}$—CH$_2$—Acr and X=Br.

In addition to the significant thermal stability, unusually large hypochromicity (around 80%) was observed upon binding of these molecules with DNA as shown in FIG. 3. These results indicate the existence of strong π-stacking interactions between the ligand molecules and DNA bases. This result in, only partial separation of DNA strands on melting, leading to a decrease in absorbance change. The large stabilization and significant hypochromicities offered by the structures of formula 1a and 1b prove further their strong interaction with DNA and potential use in biology for the detection of various DNA structures, stabilization of triplex and G-quadruplex structures.

EXAMPLE 8

Demonstration as photoactivated DNA cleaving agents. Cleavage of plasmid DNA was followed by monitoring the conversion of supercoiled (Form I) to open circular relaxed (Form II) and linear (Form III). Plasmid DNA cleavage is a very sensitive technique and when combined with several repair endonucleases, it can serve as a kind of fingerprint of the species directly responsible for the damage. Induction of one single strand break (SSB) by a compound converts Form I to Form II and the quantification of which indicates its efficiency of DNA cleavage. A DNA relaxation assay was used to quantify SSB and endonuclease-sensitive modifications (Epe, B.; Helger, J.; Wild, D. *Carcinogenesis* 1989, 10, 2019 and Epe, B.; Mftzel, P.; Adam, W. *Chem. Biol. Interactions* 1988, 67, 149). This assay makes use of the fact that Form I when converted by either a single strand break (SSB) or the incision by a repair endonuclease leads to Form II, which migrates separately in agarose gel electrophoresis.

Phosphate-buffered (pH 7.0), air-saturated solutions of PM2 DNA (10 µg/mL) at 0° C. were irradiated with 360 nm near-UV irradiation in the presence of various concentrations of acridine-viologen bifunctional molecules represented by compound of formula 1a and 1b (wherein Y=—(CH$_2$)$_n$, wherein n=1–11; R=—MV$^{2+}$—(CH$_2$)$_m$—CH$_3$X$^{\ominus}$ or —Pyr$^{2+}$—(CH$_2$)$_m$—CH$_3$X$^{\ominus}$ and wherein Y=—(CH$_2$)$_n$, wherein n=1–11; R=—MV$^{2+}$—(CH$_2$)$_m$—Acr2X$^{\ominus}$ or —Pyr$^{2+}$—(CH$_2$)$_m$—Acr2X$^{\ominus}$ respectively). Subsequently, the DNA was analyzed for the following types of modifications: (i) DNA single and double strand breaks; (ii) sites of base loss (AP sites) recognized by exonuclease III; (iii) base modifications plus AP sites sensitive to the T4 endonuclease V; (iv) base modifications plus AP sites sensitive to the endonuclease III and (v) base modifications plus AP sites sensitive to formamidopyrimidine-DNA glycosylase (FPG protein). DNA damage profile induced by the acridine-viologen bifunctional molecules are presented in FIG. 4.

It is evident from the damage profiles that both the compounds induced very few AP sites and few modifications sensitive to endonuclease III, but a large number of base modifications sensitive to FPG protein were observed. Further, no significant DNA damage was observed either by irradiation of PM2 DNA alone or in the dark in presence of viologen linked acridines at the highest concentrations, thereby indicating that the damage observed is purely initiated by the photoactivation of these compounds. Hence these compounds can be used as efficient photoactivated DNA cleaving agents.

EXAMPLE 9

Figure 5:
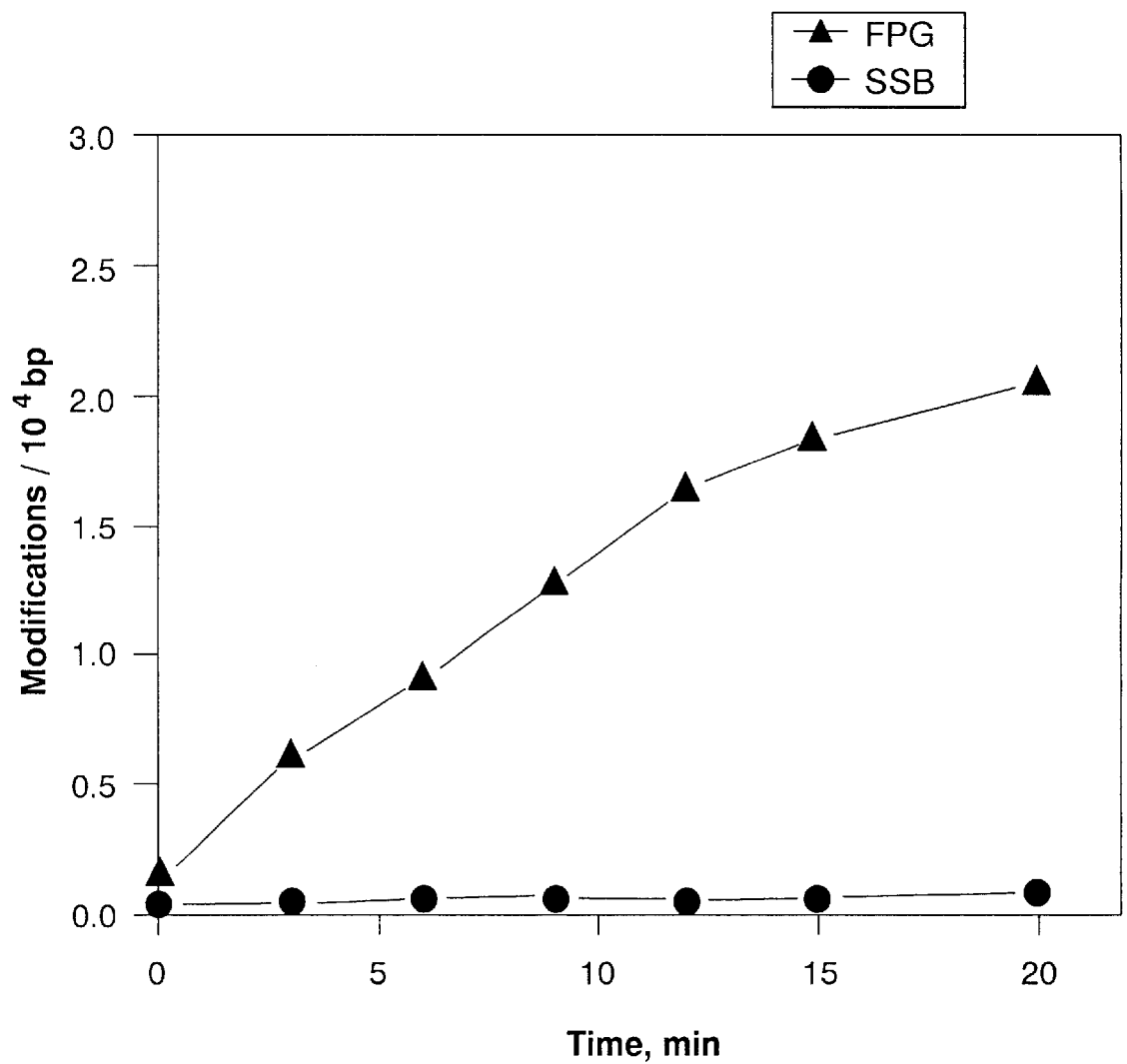
FIG. 5 shows the time dependence of DNA modifications, single strand breaks (SSB) (○) and formamidopyrimidine-DNA glycosylase (FPG protein) sensitive modifications (Δ) induced in PM2 DNA by compound of formula 1a wherein n=1, R=—MV$^{2+}$—(CH$_2$)$_3$—CH$_3$ and X=Br (0.25 μM 0° C.) upon UV irradiation with 360 nm light (4.6 kJ/m$^2$).
Figure 6:
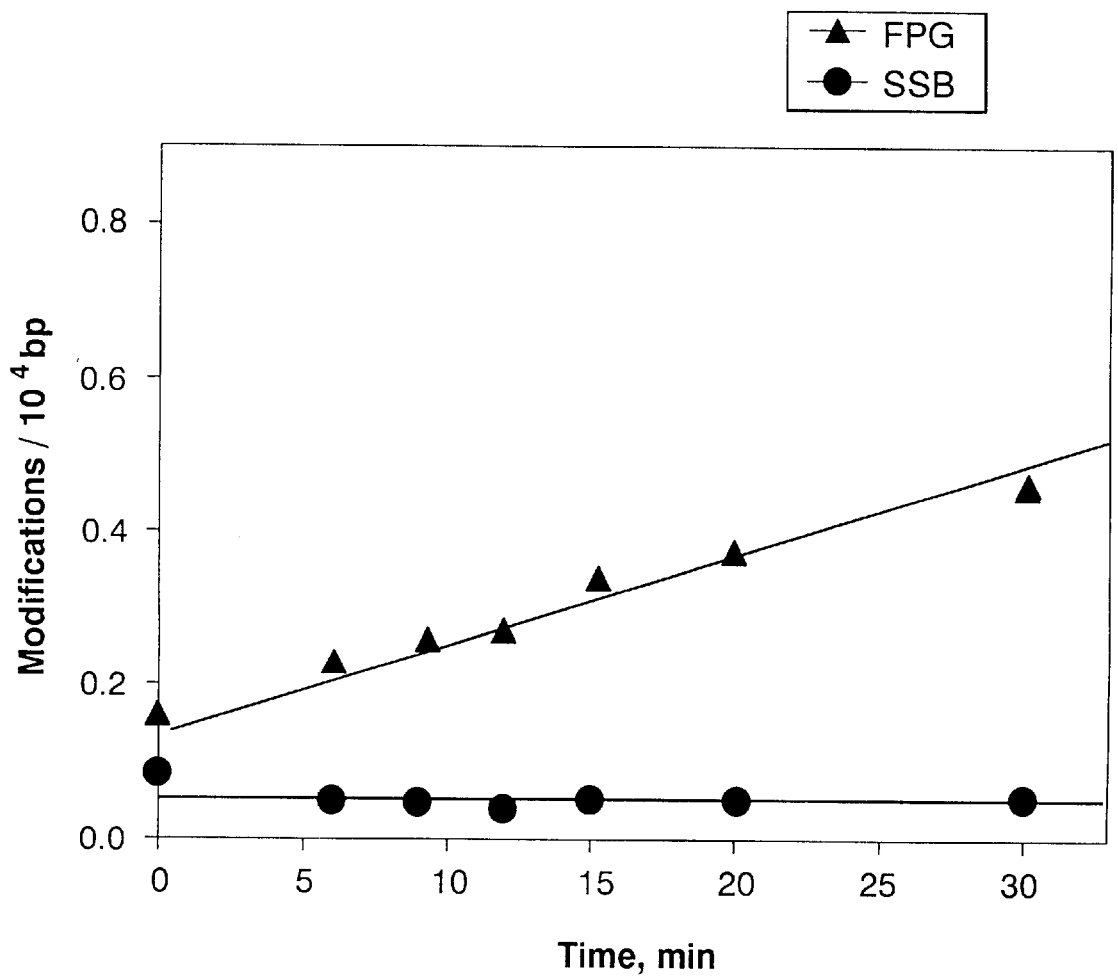
FIG. 6 shows the time dependence of DNA modifications, single strand breaks (SSB) (○) and formamidoglycosylase (FPG protein) sensitive modifications (A) induced in PM2 DNA by compound of formula 1a wherein n=11, R=—MV$^{2+}$—(CH$_2$)$_3$—CH$_3$ and X=Br (0.30 μM, 0° C.) upon UV irradiation with 360 nm light (4.6 kJ/m$^2$).
Figure 6A:
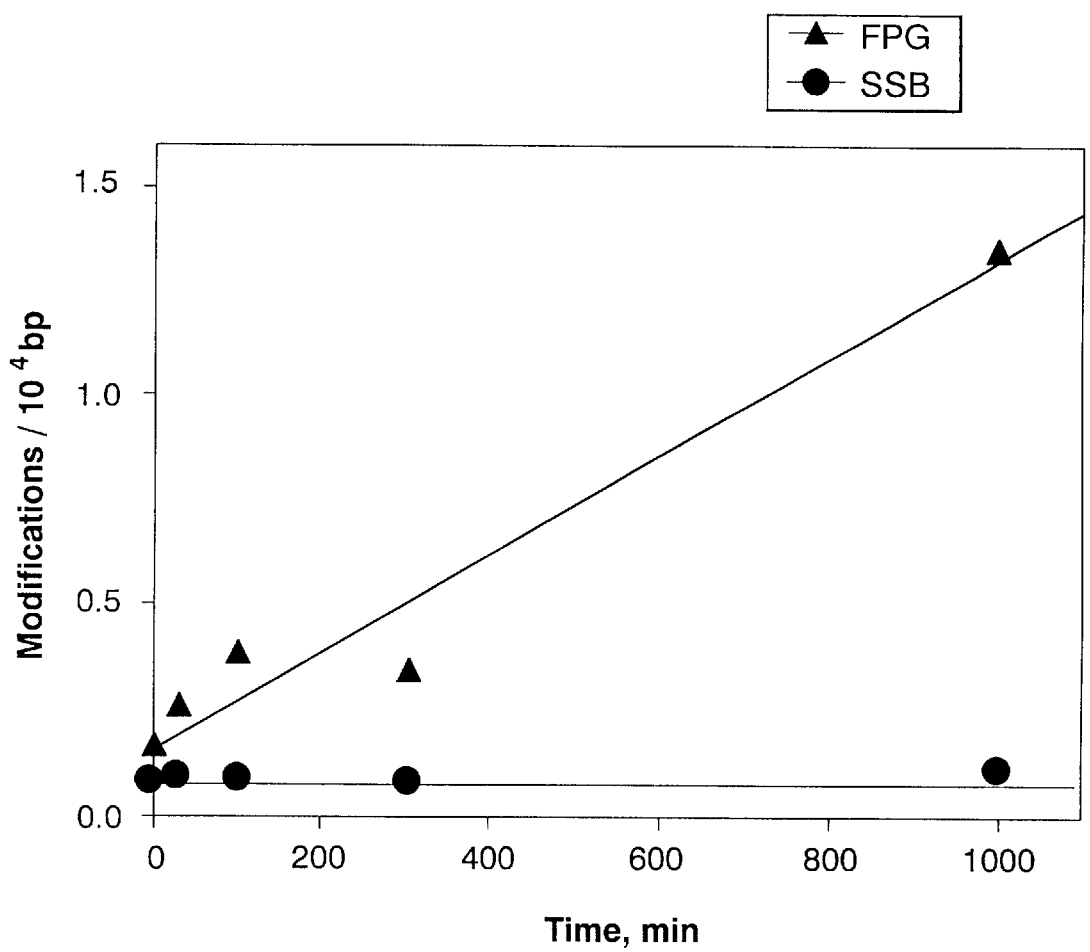

Efficiency of DNA cleavage. Since the major damage induced by the acridine-viologens is recognized by the FPG protein (FIG. 4), we have investigated the effect of irradiation time and concentration of these systems on the formation of FPG sensitive modifications and SSB. FIG. 5 and FIG. 6 show the irradiation time dependent formation of single-strand breaks (SSB) and FPG sensitive modifications induced by the acridine-viologen bifunctional derivatives compound of formula 1a (wherein n=1, R=—MV$^{2+}$—(CH$_2$)$_3$—CH$_3$ and X=Br and wherein n=11, R=—MV$^{2+}$—(CH$_2$)$_3$—CH$_3$ and X=Br), respectively. As can be seen from these figures the damage sensitive to FPG protein increases, in each case, with increase in the time of irradiation, indicating the catalytic property of these compounds. No significant increase in the generation of SSB was observed, even after the irradiation for 30 min. Similarly, increase in DNA damage was observed with the increase in concentration as shown in the inset of FIG. 6.

These results clearly demonstrate that the acridine-viologen bifunctional derivatives induce large number of base modifications sensitive to the repair endonuclease FPG protein, with little damage recognized by repair endonuclease III. FPG protein is known to recognize modifications such as 8-oxoguanosine and formamido-pyrimidines, ring-opened products of purines (Boiteux, S.; Gajewski, E.; Laval, J.; Dizdarough, M. *Biochemistry*, 1992, 31, 106). , Both 8-oxoguanosine and formamidopyrimidines can be generated in DNA by hydroxyl radicals (Epe, B.; Haring, M.; Ramaiah, D.; Stopper, H.; Abou-Elzahab, M.; Adam, W.; Saha-Moller, C. R. *Carcinogenesis* 1993, 14, 2271; Epe, B.; Pflaum, M.; Haring, M.; Hegler, J.; Rudiger, H. *Toxicol Lett.* 1993, 67, 57), singlet oxygen and by electron transfer mechanism (von Sonntag, C. *The Chemical Basis of Radiation Biology;* Taylor and Francis, London, 1987).

Figure 4:
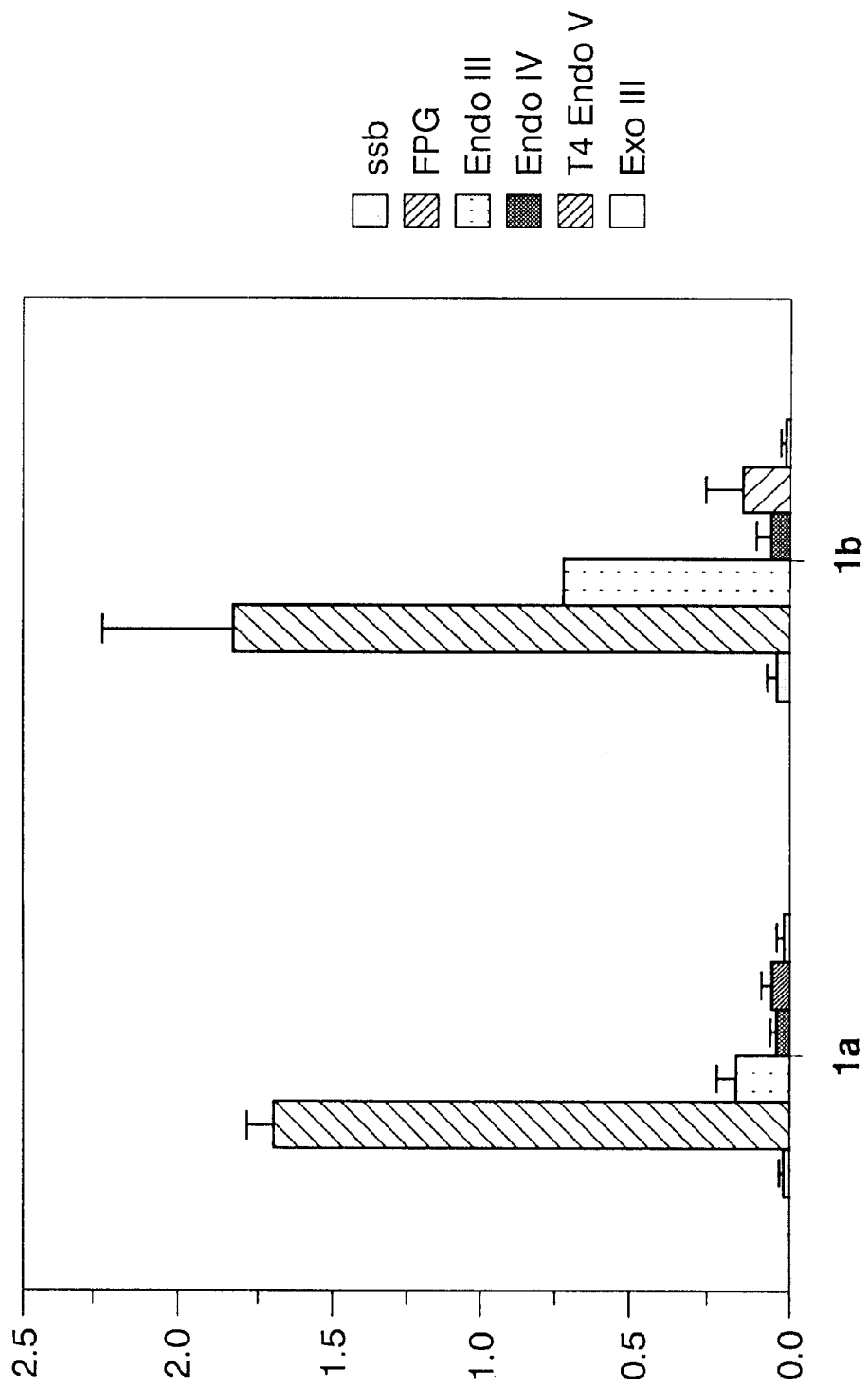
FIG. 4 shows the DNA damage profiles showing single strand breaks and various endonuclease-sensitive modifications induced in PM2 DNA by compound of formula 1a (250 nM, 18 kJ/m$^2$) wherein n=1, R=—MV$^{2-}$—(CH$_2$)$_3$—CH$_3$ and X=Br and at (1 μM, 9 kJ/m$^2$) wherein n=11, R=—MV$^{2+}$—(CH$_2$)$_3$—CH$_3$ and X=Br.

The involvement of both hydroxyl radicals and singlet oxygen can be ruled out since the damage profiles shown in FIG. 4 are different from those induced by the ionizing radiation and disodium salt of 1,4-etheno-2,3-benzoxlioxin-1,4-dipropanoic acid (Aruoma, O. I.; Halliwell, B.; Dizdaroglu, M. *J. Biol. Chem.* 1989, 264, 13024; Muller, E.; Boiteux, S.; Cunningham, R. P.; Epe, B. *Nucl. Acids Res.* 1990, 18, 5969). In addition, DNA cleavage studies were examined in presence of various additives. Results of these studies indicate that acridine-viologen bifunctional molecules can be used as reagents for induction of DNA damage purely through photoinduced electron transfer particularly for the modification (oxidation) of guanine base in DNA.

EXAMPLE 10

Demonstration of cleavage at guanine (G), preferential cleavage of 5'-G of GG sequence and G of a AG bulge. In order to examine the selectivity in cleavage and also to find out whether if there is any preferential reaction of the viologen linked acridines towards base bulges, we have analyzed the cleavage reactions using a few end labeled synthetic oligonucleotides (Table 3) by polyacrylamide gel electrophoresis (PAGE).

TABLE 3

DNA sequence

SEQ ID NO: 3  5'-*CAC TGG CTT TTC GGT GCA T-3'

SEQ ID NO: 4  5'-ATG CAC CGA AAA GCC AGT G-3'

SEQ ID NO: 5  5'-*CAC TGG CTT CCT TCG GTG CAT-3' (CC-bulge)

SEQ ID NO: 6  5'-*CAC TGG CTT AGT TCG GTG CAT-3' (AG-bulge)

Oligonucleotides SEQ ID NOS: 3, 5 (CC-bulge) and 6 (AG-bulge) were radiolabeled at 5'-OH using [$\gamma$-$^{32}$P]ATP and bacterial T4 polynucleotide kinase according to the standard procedure (Sambrook, J.; Fritsch, E. F.; Maniatis, T. *Molecular Cloning: A Laboratory Manual*, Cold Spring Harbor Laboratory Press, New York, 1989) and hybridized with the oligonucleotide SEQ ID NO: 4, incubated with various concentrations of viologen linked acridines and irradiated with a light source in microcentrifuge tubes in a Rayonet Photoreactor (RPR) containing eight 350 nm lamps according to the reported procedure (Ramaiah D.; Kan, Y.; Koch, T.; Qrum, H.; Schuster, G. B. *Proc. Nail. Acad Sci. USA* 1998, 95, 12902; Ramaiah D.; Koch, T.; Qrum, H.; Schuster, G. B. *Nucl. Acids Res.* 1998, 26, 3940). After irradiation, the samples were precipitated with buffer, washed two times with cold 70% aqueous ethanol, treated with hot piperidine for 30 mm at 90° C., lyophilized under vacuum and analyzed by PAGE. Maxam-Gilbert A/G, T and C- specific reactions were performed by routine protocols (Maxam, A. M.; Gilbert, W. *Methods in Enzymol.* 1980, 65, 499; Ramaiah D.; Kan, Y.; Koch, T.; Qrum, H.; Schuster, G. B. *Proc. Natl. Acad Sci. USA* 1998, 95, 12902).

Figure 7:
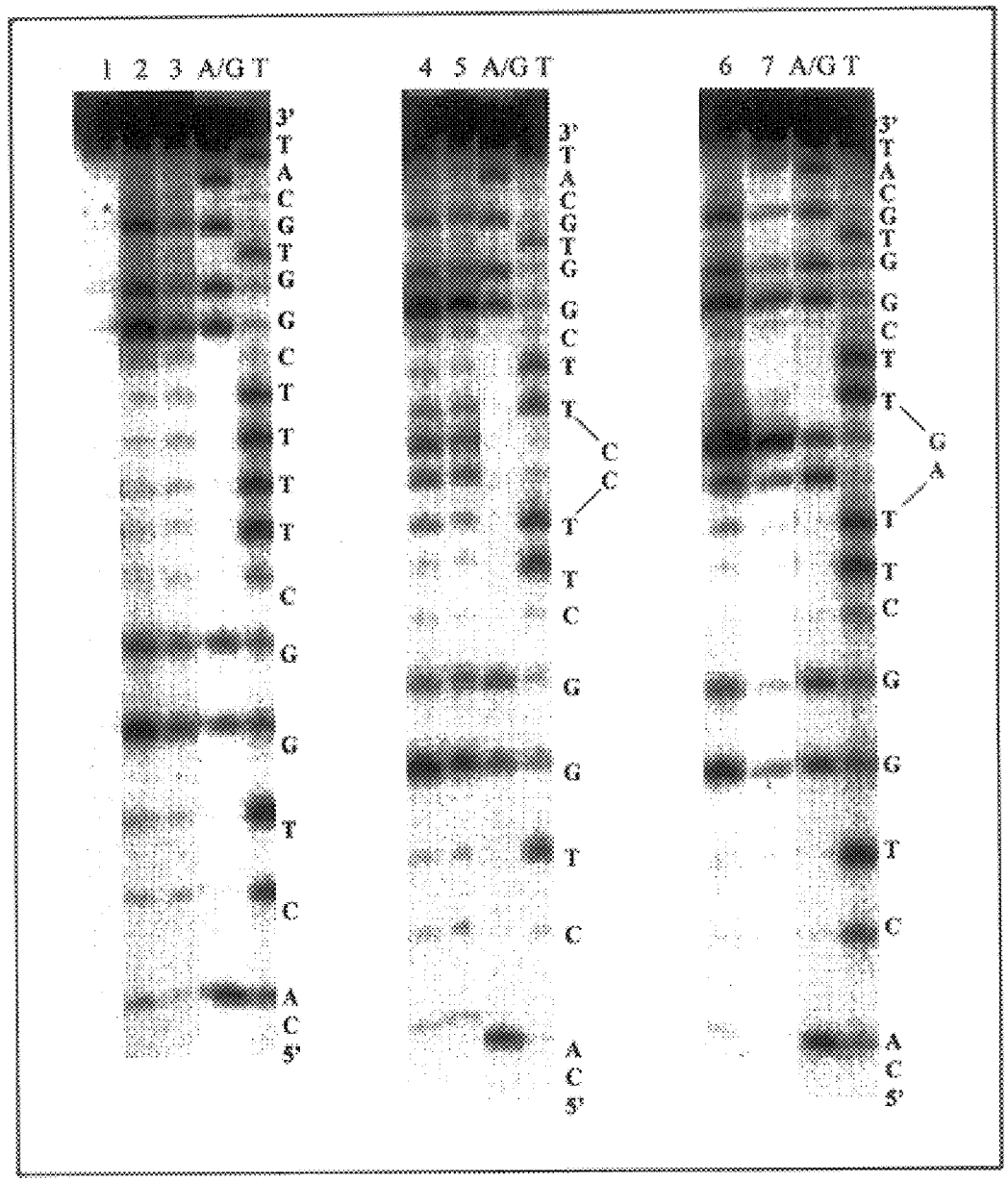
FIG. 7 shows the autoradigram of a 10% denaturing polyacrylamide gel showing photocleavage of duplex DNA

The selectivity of cleavage pattern of 5'-labeled oligonucleotides SEQ ID NOS: 3, 5 and 6 caused by the bifunctional acridine-viologen derivatives of compound of formula 1a and 1b (wherein Y=—(CH$_2$)$_n$, wherein n=1–11; R=MV$^{2-}$—(CH$_2$)$^m$—CH$_3$2X$^\ominus$ or -Pyr$^{2+}$—(CH$_2$)$_m$—CH$_3$2X$^\ominus$ and wherein Y=—(CH$_2$)$_n$, wherein n=1–11; R=—MV$^{2+}$—(CH$_2$)$_m$-Acr2X$^\ominus$ or -Pyr$^{2+}$—(CH$_2$)$_m$-Acr2X$^\ominus$, respectively) is shown in FIG. 7. Both these compounds were found to cleave the oligonucleotide SEQ ID NO: 3, at the GG sites with a significant preference for the 5'-G over the 3'-G (lanes 2 and 3 of FIG. 7). Small amount of cleavage was also observed at the G site. Similar observations were made with the oligonucleotide SEQ ID NO: 5 (CC-bulge) by both of compound of formula 1a and 1b (lanes 4 and 5 of FIG. 7). Practically no cleavage at the CC bulge site was observed. Irradiation of the oligonucleotide SEQ ID NO: 6 (AG-bulge) in the presence of compound of formula 1a and 1b (wherein Y=—(CH$_2$)$_n$, wherein n=1–11; R=—MV$^{2+}$—(CH$_2$)$_m$—CH$_3$2X$^\ominus$ or -Pyr$^{2-}$—(CH$_2$)$_m$—CH$_3$2X$^\ominus$ and wherein Y —(CH$_2$)—, wherein n=1–11; R=—MV$^{2+}$—(CH$_2$)$_m$-Acr2X$^\ominus$ or -Pyr$^{2+}$—(CH$_2$)$_m$-Acr2X$^\ominus$, respectively), caused remarkably selective cleavage at the G of the AG bulge (lanes 6 and 7 of FIG. 7). Compound of formula 1a (wherein Y=—(CH$_2$)$_n$, wherein n=1–11; R=—MV$^{2+}$—(CH$_2$)$_m$—CH$_3$2X$^\ominus$ or -Pyr$^{2+}$—(CH$_2$)$_m$—CH$_3$2X$^\ominus$) was found to be more efficient in cleaving the duplex DNA structures and also duplexes containing the base bulges. These results indicate that these molecules can be used for the photoactivated selective cleavage of 5'-G of the GG sites and G of the AG two base bulges in DNA and also for their recognition.

EXAMPLE 11

Demonstration of catalytic activity. Since the systems under investigation posses high DNA association constants and found to cleave efficiently at G sites in DNA duplex and base bulges upon irradiation, we further demonstrated their catalytic properties so that they can have potential applications in biology and industry. Direct laser excitation of the viologen linked acridine of formula 1a, 1b and 1c (wherein Y=—(CH$_2$)$_6$, wherein n=1–11; R=—MV$^{2+}$—(CH$_2$)$_m$—CH$_3$2X$^\ominus$ or —Pyr$^{2+}$—(CH$_2$)$_m$—CH$_3$2X$^\ominus$ wherein Y=—(CH$_2$)$_n$, wherein n=1–11; R=—MV$^{2+}$—(CH$_2$)$_m$—Acr2X$^\ominus$ or —Pyr$^{2+}$—(CH$_2$)$_m$—Acr2X$^\ominus$; and wherein Y=ortho or para tolyl; R=—MV$^{2+}$—(CH$_2$)$_m$—CH$_3$2X$^\ominus$ or —Pyr$^{2+}$—(CH$_2$)$_m$—CH$_3$2X$^\ominus$ respectively) in water or buffer showed no absorptions assignable to transient intermediates. However, when the laser excitation of viologen linked acridine of formula 1a (wherein Y=—(CH$_2$)$_n$, wherein n=1-11; R=—MV$^{2+}$—(CH$_2$)$_m$—CH$_3$2X$^\ominus$ or —Pyr$^{2+}$—(CH$_2$)$_m$—CH$_3$2X$^\ominus$ was carried out in water or buffer in the presence of external electron donors such as N,N-dimethylaniline (10 mM) or guanosine (1.8 mM) a transient species with absorption maxima at 395 and 610 nm, was observed. The spectral features of this transient were similar to those of methyl viologen radical cation (MV$^-$), reported in the literature (Watanabe, T.; Honda, K. *J. Phys. Chem.* 1982, 86, 3661; Kelly, L. A.; Rodgers, M. A. J. *J. Phys. Chem.* 1994, 98, 6377). Similarly, laser excitation of viologen linked acridine of formula 1a (wherein Y=—(CH$_2$)$_n$, wherein n=1–11; R=MV$^{2-}$—(CH$_2$)$_m$—CH$_3$2X$^\ominus$ or —Pyr$^{2+}$—(CH$_2$)$_m$—CH$_3$2X$^\ominus$) in the presence of DNA in water or buffer, gave a transient species assignable to the reduced methyl viologen (FIG. 8).

These results clearly show that the excited acridine chromophore transfers an electron to the viologen moiety leading to the formation of radical cation of acridine and reduced methyl viologen The radical cation of acridine once formed, oxidizes the electron donor present in the medium (the formation of methyl viologen radical cation (MV$^+$) is facilitated by external sacrificial electron donors) and reverts back to acridine for reabsorption of photons. The reduced methyl viologen can in turn transfer an electron to the molecular oxygen thereby reverting back to methyl viologen and generating superoxide radical anion. Therefore, these bifunctional molecules and derivatives thereof can function as catalytic photoactivated DNA cleaving agents in presence of sacrificial electron donors and as catalysts for the oxidation of water under appropriate conditions to generate hydrogen in industrial applications.

Bifunctional molecules of the present invention posses excellent properties of a photosensitizer for phototherapeutical as well as catalytic photoactivated DNA cleaving and industrial applications. The main advantages of the present systems include:

1. Compounds represented by formula 1 (1a, 1b, 1c and 1d) are pure single substances.
2. Their synthetic methodology is very economical.

3. They are very stable, highly soluble in aqueous medium and exist in the neutral form under physiological conditions.
4. These compounds posses good absorption properties and are very stable in the dark and under irradiation conditions.
5. They constitute an effective donor-acceptor system and their redox properties can be tuned as a function of pH and spacer group.
6. They form a novel class of compounds with high affinity to DNA and interact with DNA through intercalation, bisintercalation and groove binding.
7. These systems stabilize various structures of DNA including duplex DNA, base bulges, triplex and quadruplex DNA structures.
8. These systems can be easily covalently linked to oligonucleotides for the stabilization of triplex DNA and also for the selective photocleavage of DNA.
9. These systems posses special affinity for A.T sequence and hence can have potential applications as probes for the detection of such sequences in DNA
10. They form a novel class of compounds, which cleave DNA in a catalytic way under irradiation conditions and act as catalytic photoactivated DNA cleaving agents.
11. They cleave DNA purely through the photoinduced electron transfer mechanism and selectively at guanine sites and with excellent selectivity at 5'-G of GG sequence in DNA.
12. They cleave duplex DNA containing AG base bulges selectively at G sites and hence act as probes for the detection of AG bulge containing DNA sequence.
13. These systems form a novel class of photosensitizers, which upon irradiation in presence of external donors results in an effective charge separation and hence these systems and derivatives thereof can act as photocatalysts in industrial applications including in the photoinduced hydrogen generation from water.

We claim:

1. A viologen linked acridine based molecule of the formula 1 (1a, 1b, 1c, 1d) below:

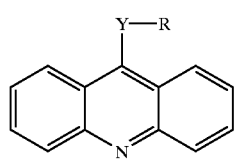

1a. wherein
 Y=—(CH$_2$)$_n$—; n=1–11;
 R=—MV$^{2+}$—(CH$_2$)$_m$—CH$_3$ 2X$^\ominus$ or -Pyr$^{2+}$—(CH$_2$)$_m$—CH$_3$ 2X$^\ominus$; m=1–13

1b. wherein
 Y=—(CH$_2$)$_n$—; n=1–11;
 R=—MV$^{2+}$—(CH$_2$)$_m$-Acr 2X$^\ominus$ or -Pyr$^{2+}$—(CH$_2$)$_m$-Acr 2X$^\ominus$; m=1–11

1c. wherein
 Y=ortho or para tolyl
 R=—MV$^{2+}$—(CH$_2$)$_m$—CH$_3$ 2X$^\ominus$ or -Pyr$^{2+}$—(CH$_2$)$_m$-CH$_3$ 2X$^\ominus$; m=1–13

1d. wherein
 Y=—(CH$_2$)$_n$—; n=5 or 10
 R=-Acr$^+$ CH$_3$2I$^\ominus$; wherein N in the acridine main ring is also quaternized by alkyl group and wherein Formula 1

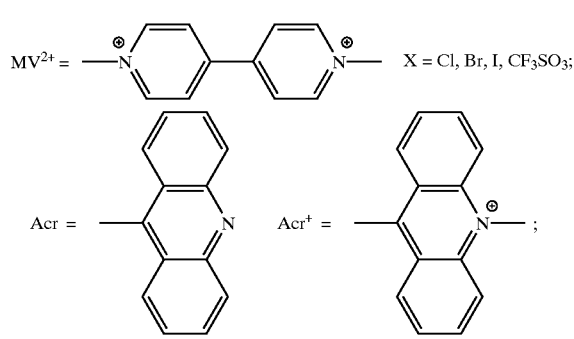

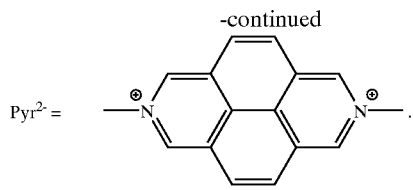

2. A process for the preparation of a viologen linked acridine based molecule of the formula 1a below:

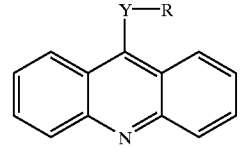

wherein
 Y=—(CH$_2$)$_n$—; n=1–11;
 R=MV$^{2+}$—(CH$_2$)$_m$—CH$_3$ 2X$^\ominus$; or -Pyr$^{2+}$—(CH$_2$)$_m$—CH$_3$ 2X$^\ominus$; m=1–13 and
and wherein

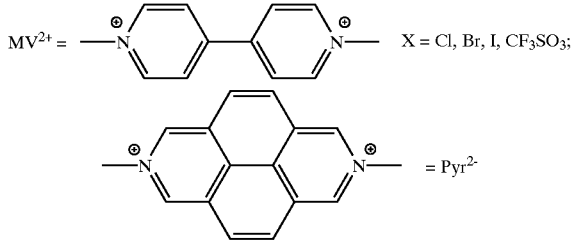

comprising forming a solution of ω-(acridin-9-yl)-α-bromoalkanes and 1-alkyl-4,4'-bipyridinium bromides in dry acetonitrile in the ratio of 1:1, stirring the above solution at a temperature in the range of 20–50° C. for a time period in the range between 8–24 h to obtain a precipitate, filtering, and washing the precipitate with dry acetonitrile and dichloromethane to remove any unreacted starting materials, purifying the solid so obtained to give the compound of formula 1a.

3. A process as claimed in claim 2 wherein the compound of formula 1 is recrystallized from ethyl acetate, methanol, dry acetonitrile, dichloromethane or any mixture thereof.

4. A process as claimed in claim 3 wherein the compound of formula 1 is recrystallized from a mixture of methanol and acetonitrile in a ratio of 1:4.

5. A method for photoactivated cleavage of a DNA comprising administering to a human or animal in need thereof an effective amount of the viologen linked acridine based molecule of claim 1 and irradiating the DNA in the human being or an animal in the presence said molecule.

6. The method of claim 5, wherein the DNA is irradiated with a near-UV light.

7. The method of claim 5, wherein the photoactivated cleavage of the DNA is sequence-specific.

8. A process for the preparation of the viologen linked acridine-based molecule of the formula 1d below:

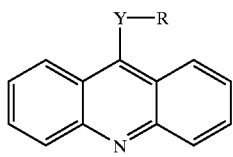

wherein
Y=—(CH$_2$)$_n$—; n=5 or 10
R=-Acr⁻CH$_3$2I$^\ominus$; wherein N in the acridine main ring is also quaternized by alkyl group
and wherein

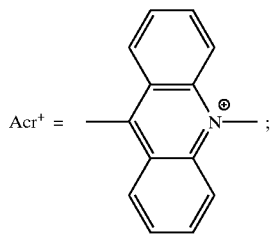

comprising forming a solution of α,ω-bis(9-acridinyl)alkane and alkyl halide in dry acetonitrile in the ratio of 1:3, stirring the above solution at a temperature in the range of 20–50° C. for a time period in the range between 8–24 h to obtain a precipitate, filtering, and washing the precipitate with dry acetonitrile and dichloromethane to remove any unreacted starting materials, purifying the solid so obtained to obtain the compound of formula 1d.

9. The process of claim 8, wherein the compound of formula id is recrystallized from ethyl acetate, methanol, dry acetonitrile, dichloromethane, or any mixture thereof.

10. The process of claim 8, wherein the compound of formula id is recrystallized from a mixture of ethyl acetate and acetonitrile in a ratio of 1:4.

11. A process for the preparation of viologen linked acridine based molecule of the formula 1b below:

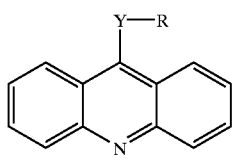

wherein
Y=—(CH$_2$)$_n$—; n=1–11;
R=—MV$^{2+}$—(CH$_2$)$_m$-Acr 2X$^\ominus$; m=1–11
and wherein

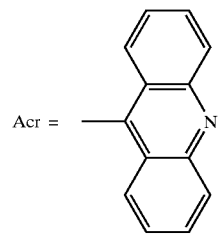

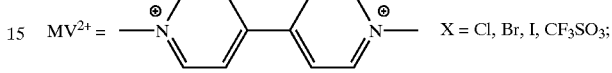

comprising forming a solution of ω-(acridin-9-yl)-α-bromoalkanes and 4,4'-bipyridine in the ratio of 2:1 in dry acetonitrile, stirring the above solution at a temperature in the range of 20–50° C. for a time period in the range between 8–24 h to obtain a precipitate, filtering, and washing the precipitate with dry acetonitrile and dichloromethane to remove any unreacted starting materials, purifying the solid so obtained to give the compound of formula 1b.

12. A process for the preparation of viologen linked acridine based molecule of the formula 1c below:

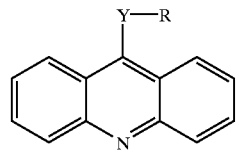

wherein
Y=ortho or para tolyl
R=—MV$^{2+}$—(CH$_2$)$_m$—CH$_3$ 2X$^\ominus$; m=1–13
and wherein

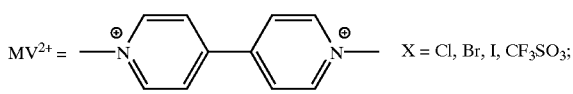

comprising forming a solution of bromomethylphenyl-acridine and 1-alkyl-4,4'-bipyridinium A bromides in dry acetonitrile in the ratio of 1:1, stirring the above solution at a temperature in the range of 20–50° C. for a time period in the range between 8–24 h to obtain a precipitate, filtering, and washing the precipitate with dry acetonitrile and dichloromethane to remove any unreacted starting materials, purifying the solid so obtained to give the compound of formula 1c.

* * * * *